(12) United States Patent
Ueda et al.

(10) Patent No.: US 10,406,342 B2
(45) Date of Patent: Sep. 10, 2019

(54) MEDICAL CONNECTOR COUPLING ASSISTING TOOL AND MEDICAL CONNECTOR SET

(71) Applicant: TERUMO KABUSHIKI KAISHA, Tokyo (JP)

(72) Inventors: Yasuhiro Ueda, Yamanashi (JP); Akifumi Yoshikawa, Yamanashi (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 17 days.

(21) Appl. No.: 15/398,450

(22) Filed: Jan. 4, 2017

(65) Prior Publication Data
US 2017/0113031 A1 Apr. 27, 2017

Related U.S. Application Data

(63) Continuation of application No. PCT/JP2015/003232, filed on Jun. 26, 2015.

(30) Foreign Application Priority Data

Jul. 4, 2014 (JP) ................................. 2014-138792
Mar. 25, 2015 (WO) ................. PCT/JP2015/001700

(51) Int. Cl.
*A61M 39/10* (2006.01)
*A61M 39/22* (2006.01)
*A61M 39/00* (2006.01)

(52) U.S. Cl.
CPC ........ *A61M 39/1011* (2013.01); *A61M 39/22* (2013.01); *A61M 39/223* (2013.01);
(Continued)

(58) Field of Classification Search
CPC ............ A61M 39/1011; A61M 39/223; A61M 39/22; A61M 2039/229; A61M 2039/0027; A61M 2209/04
See application file for complete search history.

(56) References Cited

U.S. PATENT DOCUMENTS 3,521,332 A * 7/1970 Kramer ..................... F16B 2/22
248/229.26
4,734,091 A * 3/1988 Boyle ................. A61F 9/00736
137/883
(Continued)

FOREIGN PATENT DOCUMENTS

JP   H01-133936 U   9/1989
JP   H06-042679 Y2  11/1994
(Continued)

OTHER PUBLICATIONS

English-Language Machine Translation of Japanese Patent Publication No. 5607637 B2 published Oct. 15, 2014.
(Continued)

*Primary Examiner* — Amber R Stiles
(74) *Attorney, Agent, or Firm* — Foley & Lardner LLP

(57) ABSTRACT

A medical connector coupling assisting tool for use with a lock connector part interconnecting at least two medical connectors, each of which includes a construction part, includes: at least two insertion parts configured to be inserted into respective portions defined by the constriction parts such that the insertion parts are thereby detachably mounted on the constriction parts; and a coupling part formed integrally with the at least two insertion parts and coupling the insertion parts together.

21 Claims, 26 Drawing Sheets

(52) U.S. Cl.
CPC ............. *A61M 2039/0027* (2013.01); *A61M 2039/229* (2013.01); *A61M 2209/04* (2013.01)

(56) References Cited

U.S. PATENT DOCUMENTS

| | | | |
|---|---|---|---|
| 4,826,486 A | 5/1989 | Palsrok et al. | |
| 4,837,899 A * | 6/1989 | Young | A47L 9/248 24/16 R |
| 5,460,204 A | 10/1995 | Rossi | |
| 5,695,232 A * | 12/1997 | Tipp | A45F 5/10 206/150 |
| 5,735,562 A * | 4/1998 | Borg | B65D 71/50 206/151 |
| 6,298,525 B1 * | 10/2001 | Margo | F16L 3/237 24/336 |
| 6,715,810 B2 * | 4/2004 | Borg | B65D 71/50 206/151 |
| 8,585,096 B2 * | 11/2013 | Schnell | A61M 39/1011 285/114 |
| 8,888,398 B2 * | 11/2014 | Werth | A61M 39/1011 285/365 |
| 9,097,370 B2 * | 8/2015 | Schnell | A61M 39/1011 |
| 9,433,769 B2 * | 9/2016 | Bayly | A61M 39/10 |
| 2008/0103484 A1 | 5/2008 | Hishikawa et al. | |
| 2014/0034169 A1 * | 2/2014 | Harton | A61M 5/1418 137/798 |
| 2014/0035273 A1 * | 2/2014 | Schnell | A61M 39/1011 285/92 |
| 2014/0152000 A1 * | 6/2014 | Chen | F16L 3/237 285/124.1 |
| 2014/0257235 A1 * | 9/2014 | Mobassery | A61M 39/20 604/500 |
| 2016/0208972 A1 * | 7/2016 | Lewis | F16L 37/0841 |

FOREIGN PATENT DOCUMENTS

| | | |
|---|---|---|
| JP | H07-067968 A | 3/1995 |
| JP | 1140001 S | 4/2002 |
| JP | 2010-035873 A | 2/2010 |
| JP | 3166297 U | 2/2011 |
| WO | WO-2006/068211 A1 | 6/2006 |
| WO | WO-2011/024725 A1 | 3/2011 |

OTHER PUBLICATIONS

International Search Report issued in International Patent Application No. PCT/JP2015/001700 dated Jun. 23, 2015.
International Search Report issued in International Patent Application No. PCT/JP2015/003232 dated Aug. 18, 2015.

* cited by examiner

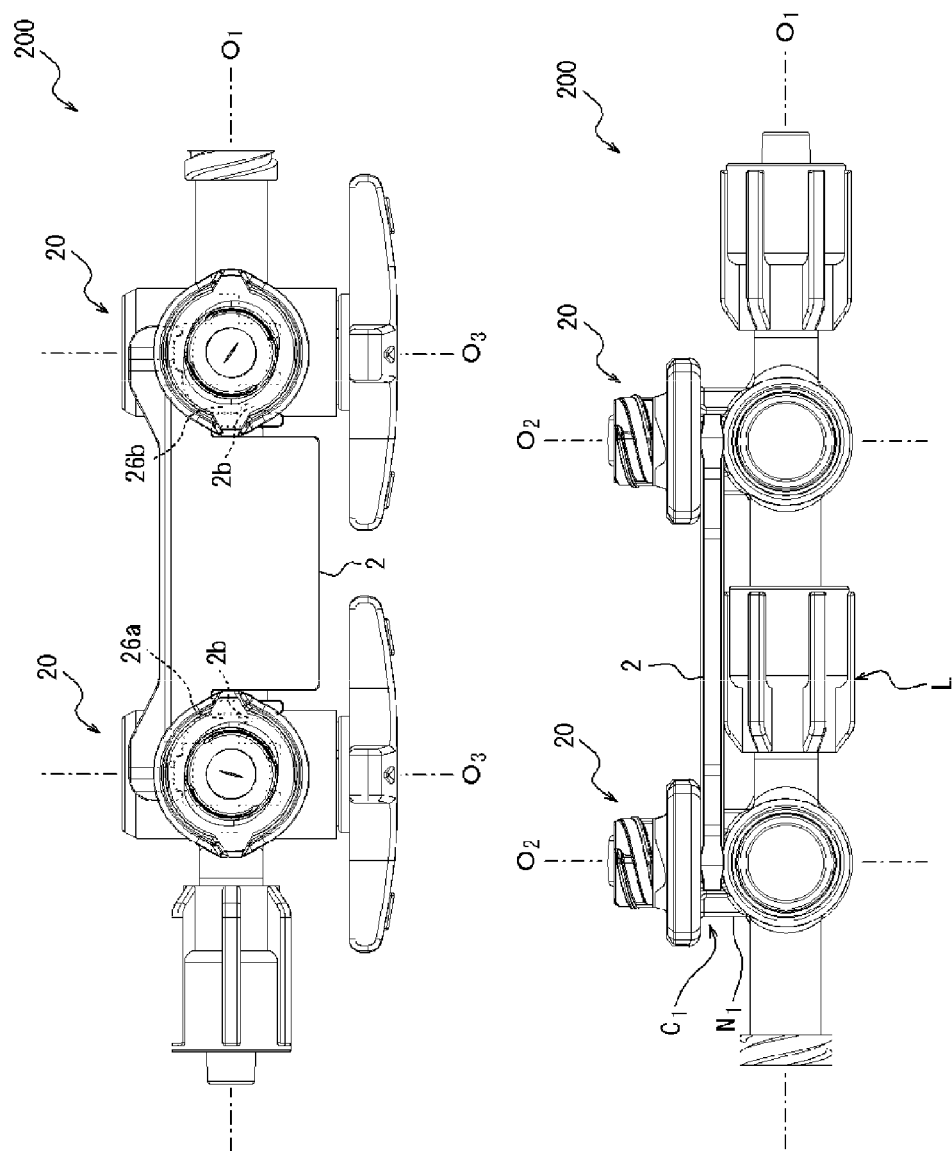

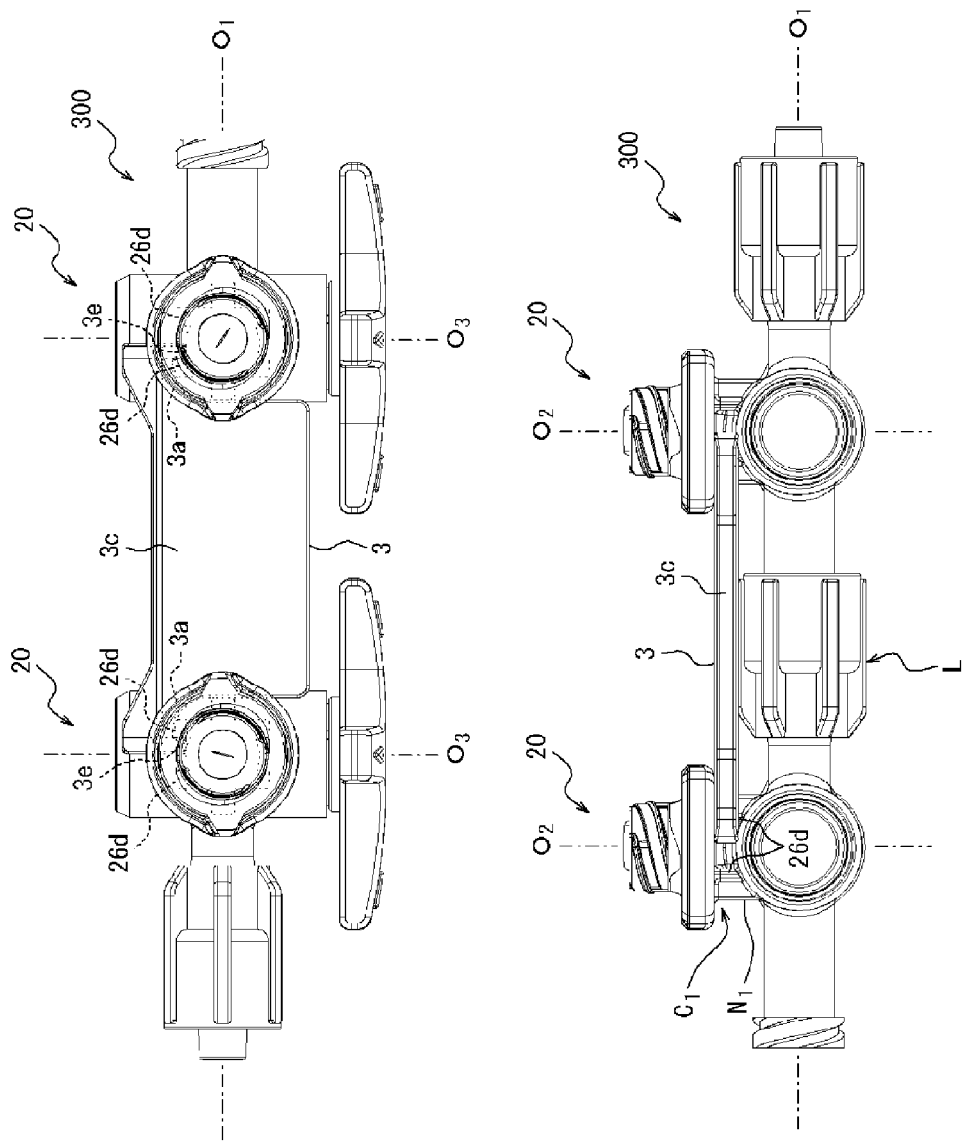

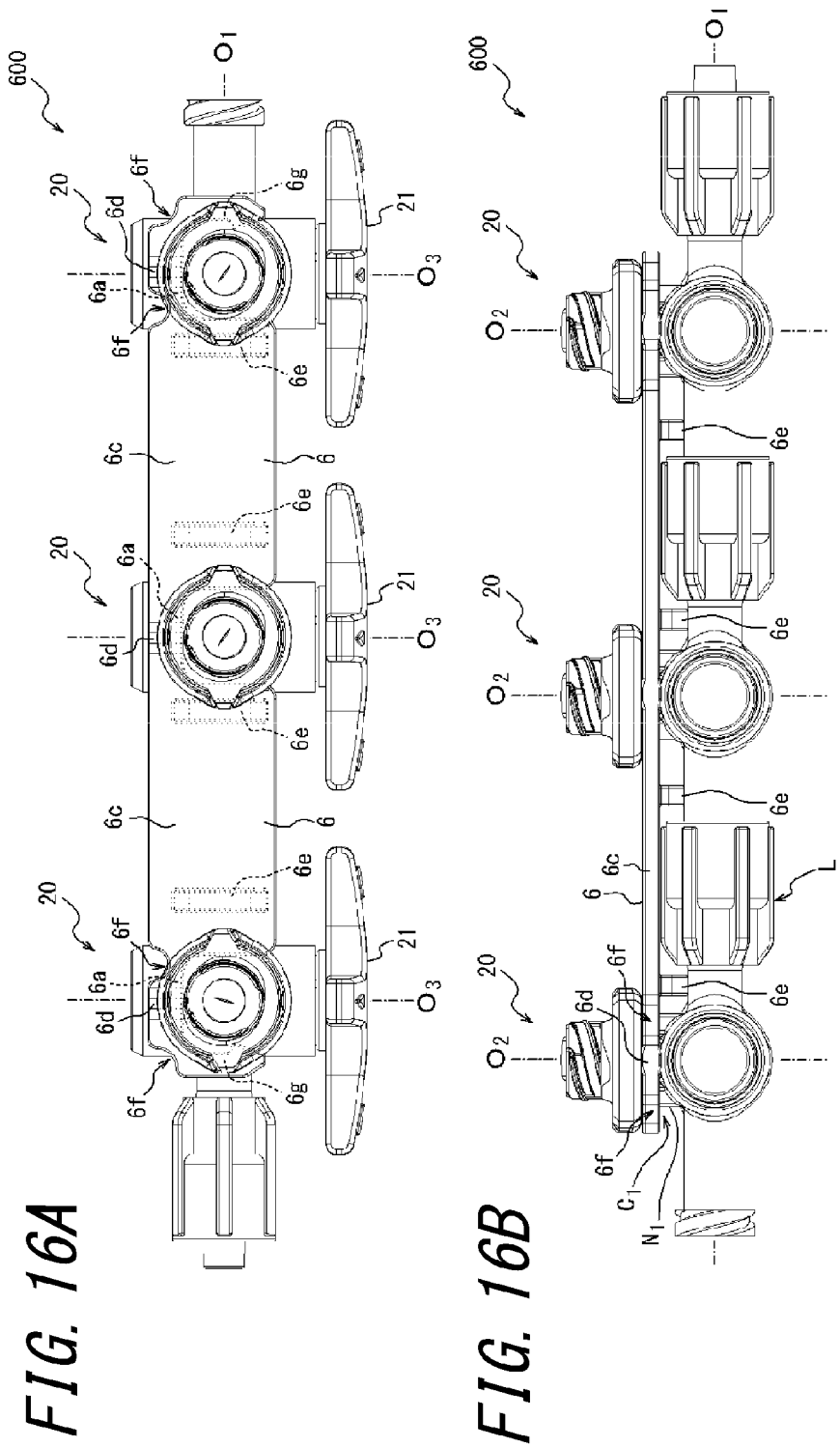

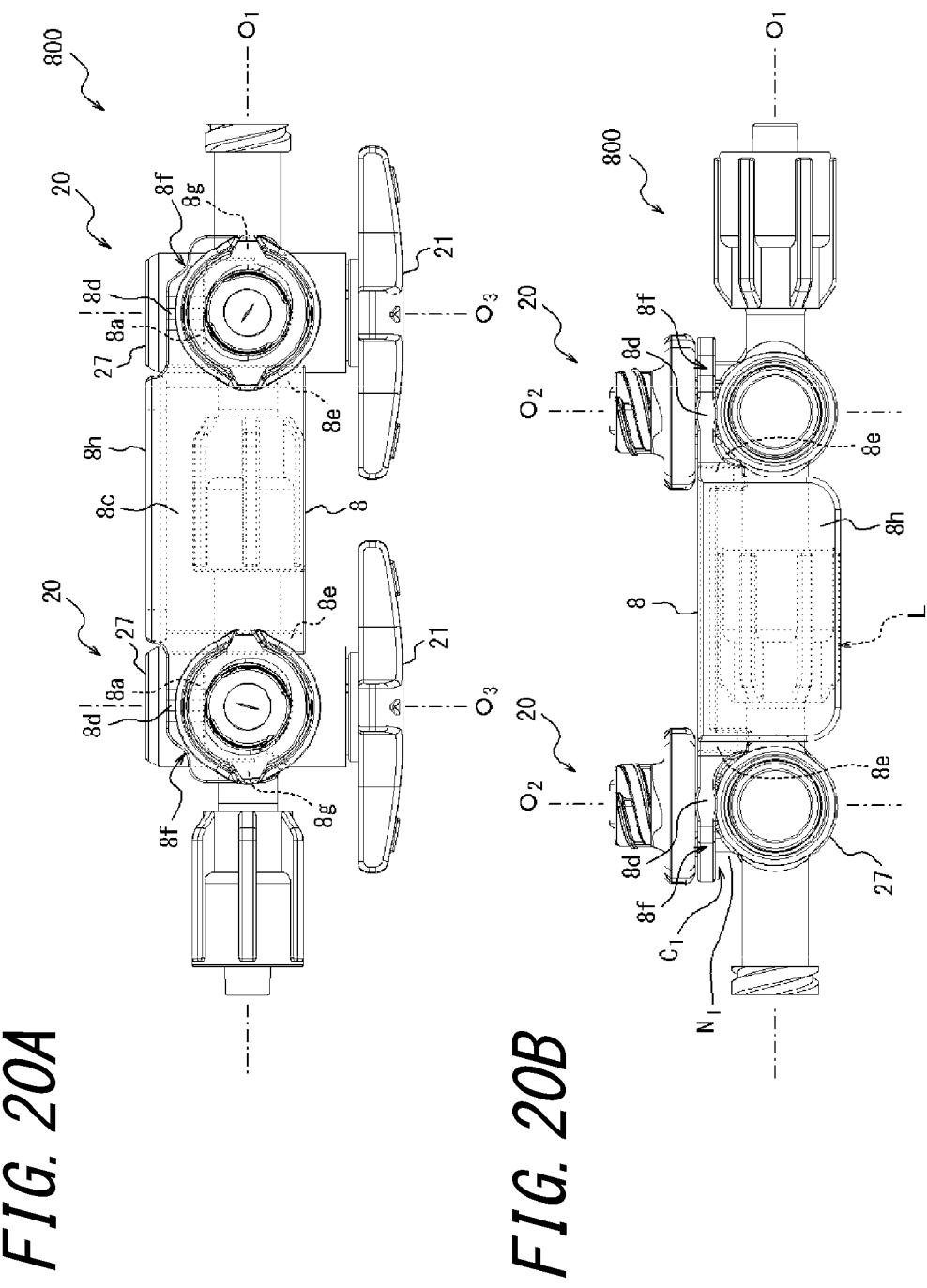

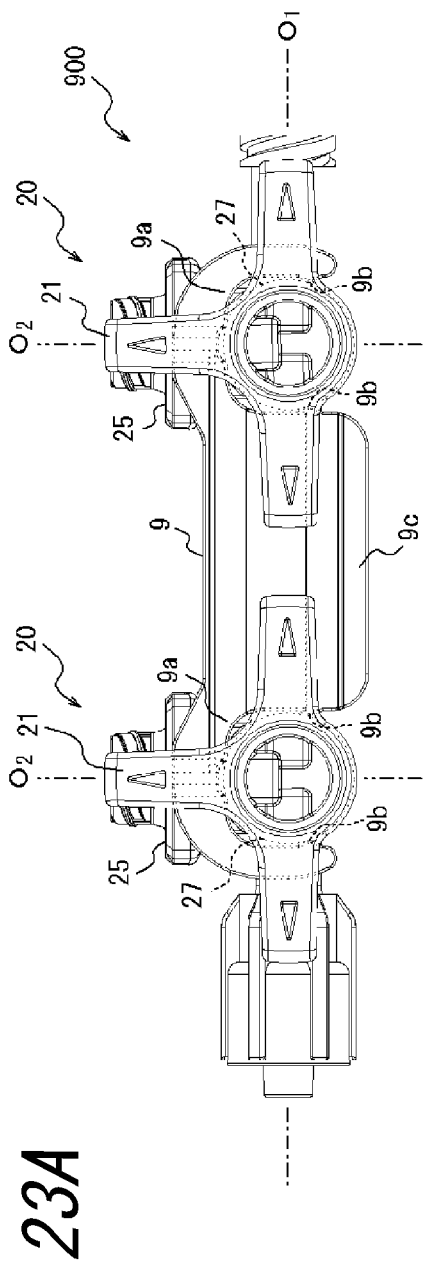
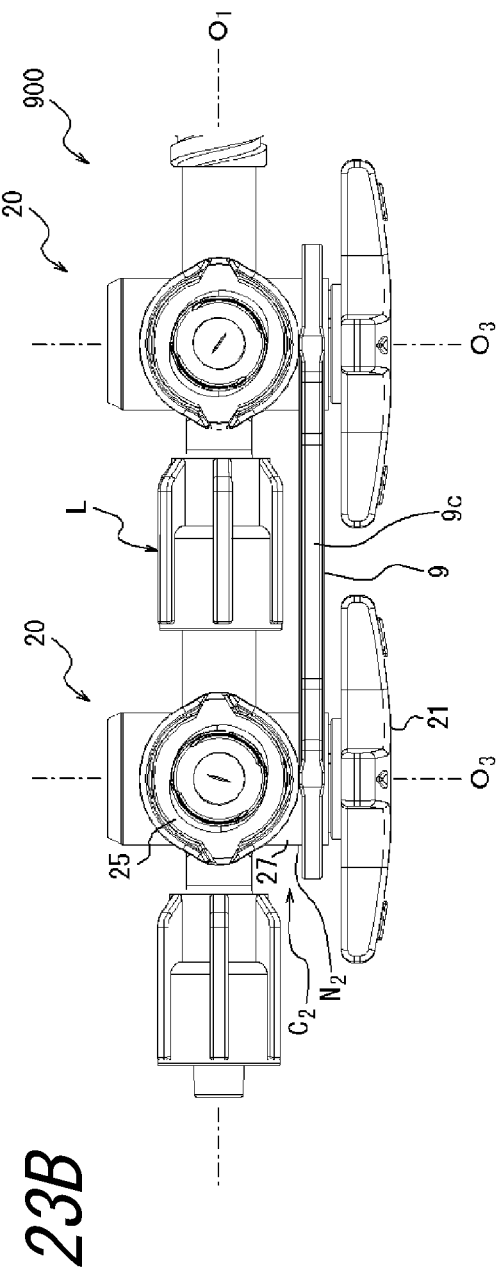
FIG. 23A
FIG. 23B

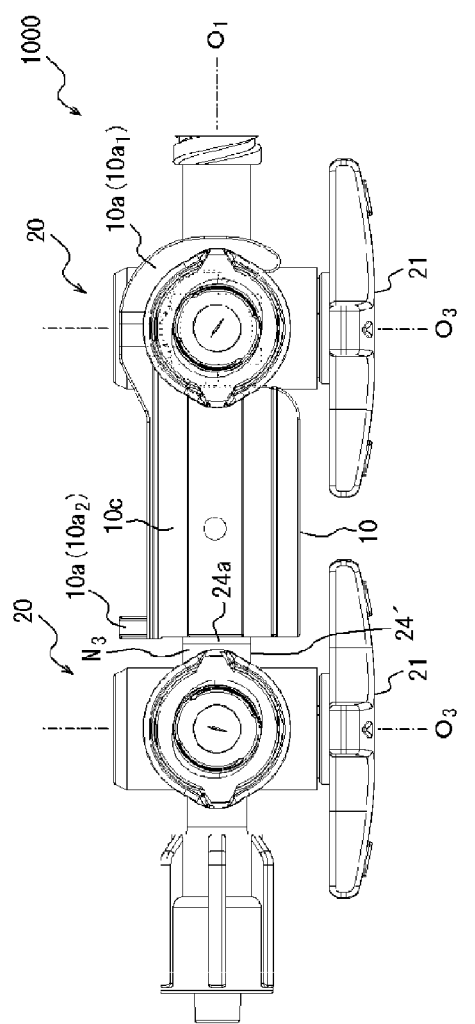
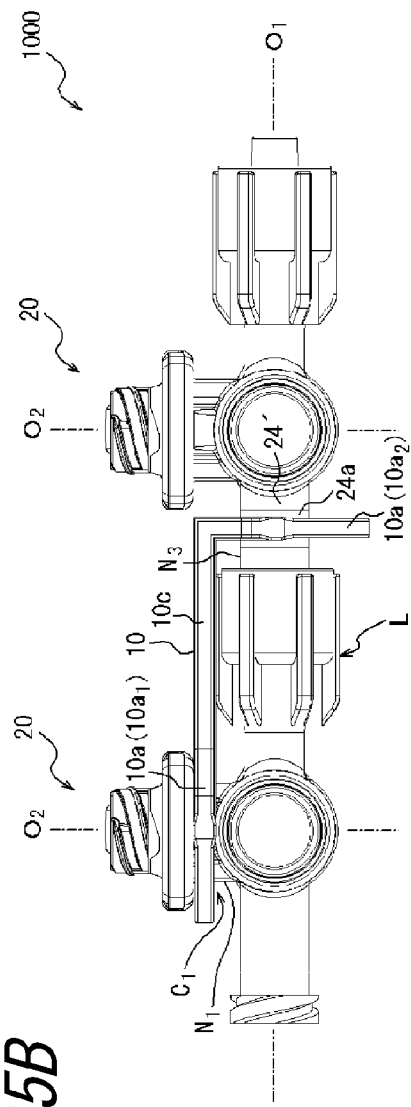
FIG. 25A
FIG. 25B

MEDICAL CONNECTOR COUPLING ASSISTING TOOL AND MEDICAL CONNECTOR SET

CROSS-REFERENCE TO RELATED APPLICATIONS

The present application is a bypass continuation of PCT Application No. PCT/JP2015/003232, filed on Jun. 26, 2015, which claims priority to PCT Application No. PCT/JP2015/001700, filed on Mar. 25, 2015, which claims priority to Japanese Application No. 2014-138792 filed on Jul. 4, 2014. These applications are hereby incorporated by reference in their entireties.

BACKGROUND

The present disclosure relates to a medical connector coupling assisting tool configured to suppress looseness of a lock connector part interconnecting at least two medical connectors. Specifically, certain embodiments of the present invention more reliably provide for relaxation of the required dimensional accuracy and suppression of the looseness of the lock connector part.

The present disclosure also relates to a medical connector set including the medical connectors and the medical connector coupling assisting tool.

Conventionally, plate members, as described in JP 07-67968 A, for example, are known for use as a medical connector coupling assisting tool. JP 07-67968 A describes a set that includes two plate members fixed to respective two medical connectors capable of being interconnected via a lock connector part. The medical connectors are coupled to each other by the lock connector part, and the plate members are fit with and connected to each other, whereby looseness of the lock connector part is suppressed.

SUMMARY

However, the plate members described in JP 07-67968 need to achieve not only the coupling between the medical connectors but also the coupling between the plate members that are fit with each other. Therefore, high dimensional accuracy is required. If a product that does not conform to this dimensional accuracy is used, the looseness of the lock connector part cannot be suppressed, and even worse, the lock connector part might not be fully fastened.

Certain embodiments of the present invention have been developed to solve the above-mentioned problem, and one object thereof is to provide a medical connector coupling assisting tool configured to suppress looseness of a lock connector part interconnecting at least two medical connectors, and specifically to provide a medical connector coupling assisting tool capable of relaxing required dimensional accuracy and suppressing the looseness of the lock connector part more reliably.

Another object of certain embodiments of the present invention is to provide a medical connector set including the medical connectors and the medical connector coupling assisting tool.

A medical connector coupling assisting tool according to one embodiment of the present invention is configured to suppress looseness of a lock connector part interconnecting at least two medical connectors, wherein each of the medical connectors includes a constriction part, and the medical connector coupling assisting tool includes: at least two insertion parts configured to be inserted into respective portions defined by the constriction parts to be detachably mounted on the constriction parts; and a coupling part formed integrally with the at least two insertion parts to couple the insertion parts together.

In one aspect, the medical connector coupling assisting tool is configured such that each of the medical connectors includes the constriction part that is aligned in parallel with an axis of the lock connector part in the interconnected state.

In one aspect, the medical connector coupling assisting tool is configured such that the medical connectors include the constriction part that is located in parallel with an axis of the lock connector part and the constriction part that is located perpendicular to the axis in the interconnected state.

In one aspect, the medical connector coupling assisting tool is configured such that the portion defined by the constriction part is a recessed part.

In one aspect, the medical connector coupling assisting tool is configured such that each of the constriction parts includes an axis orthogonal to the axis of the lock connector part, and the recessed part defined by the constriction part is provided around the axis of the constriction part, and each of the insertion parts is arranged across the axis of the lock connector part when seen along the axis of the constriction part in a mounted state on the constriction part. As used herein, "the recessed part defined by the constriction part is provided around the axis of the constriction part" includes, needless to say, such an aspect that the recessed part is provided over the entire circumference around the axis of the constriction part, and further includes such an aspect that the recessed part is provided over only a portion of a circumferential region.

In one aspect, the medical connector coupling assisting tool is configured such that each of the medical connectors includes a mixed injection port to which another medical connector is capable of being coupled via a valve body, and the constriction part is formed at the mixed injection port.

In one aspect, the medical connector coupling assisting tool is configured to include a plate member having a cutout part defining each of the insertion parts.

In one aspect, the medical connector coupling assisting tool is configured such that the plate member has three of the cutout parts.

In one aspect, the medical connector coupling assisting tool is configured such that the medical connector coupling assisting tool includes a plate member having two cutout parts defining the respective two insertion parts, and one of the two insertion parts of the plate member is attachable to or detachable from the constriction part on which the other of the two insertion parts of another plate member having the same configuration has been mounted.

In one aspect, the medical connector coupling assisting tool is configured such that the one and the other of the two insertion parts of the plate member are provided on different levels.

In one aspect, the medical connector coupling assisting tool is configured such that the plate member has at least one reinforcing rib between the cutout parts, and the reinforcing rib extends perpendicular to the axis of the lock connector part, with the insertion part mounted on each of the constriction parts.

In one aspect, the medical connector coupling assisting tool is configured such that the insertion part includes at least one cut.

In one aspect, the medical connector coupling assisting tool is configured such that an overhanging part arranged along an end edge of the plate member and extending in a direction intersecting the plate member is provided between the cutout parts of the plate member.

In one aspect, the medical connector coupling assisting tool is configured such that each of the insertion parts has a claw part that detachably locks the insertion part to the constriction part.

A medical connector set of the present invention includes any of the above-mentioned at least two medical connectors and medical connector coupling assisting tool.

By means of a medical connector coupling assisting tool according to certain embodiments of the present invention, while at least two medical connectors are interconnected by a lock connector part, at least two insertion parts are inserted into respective portions defined by constriction parts of the medical connectors. Consequently, looseness of the lock connector part can be suppressed by the insertion parts mounted on the respective constriction parts and a coupling part coupling the insertion parts together. Because the at least two insertion parts and the coupling part are integrally formed, the conventional coupling in which plate members are fit with each other is not necessary. Therefore, required dimensional accuracy can be relaxed.

Thus, according to certain embodiments of the present invention, it is possible to provide a medical connector coupling assisting tool configured to suppress the looseness of the lock connector part interconnecting the at least two medical connectors, and specifically to provide the medical connector coupling assisting tool in which it is possible to more reliably relax the required dimensional accuracy and suppress the looseness of the lock connector part.

According to one embodiment of the present invention, it is also possible to provide a medical connector set including the medical connectors and the medical connector coupling assisting tool.

BRIEF DESCRIPTION OF THE DRAWINGS

FIG. 5A is a plan view and FIG. 5B is a forward perspective view.

FIG. 6A is a plan view and FIG. 6B is a back view.

FIG. 7A is a plan view and FIG. 7B is a forward perspective view.

FIGS. 8A and 8B are views illustrating the medical connector coupling assisting tool illustrated in FIGS. 7A and 7B mounted on the two medical connectors illustrated in FIG. 1, where FIG. 8A is a plan view and FIG. 8B is a back view.

FIG. 9A is a plan view and FIG. 9B is a forward perspective view.

FIGS. 10A and 10B are views illustrating the medical connector coupling assisting tool illustrated in FIGS. 9A and 9B mounted on the two medical connectors illustrated in FIG. 1, where FIG. 10A is a plan view and FIG. 10B is a back view.

FIG. 11A is a bottom view and FIG. 11B is a perspective view seen from a bottom side.

FIG. 12A is a plan view and FIG. 12B is a back view.

FIG. 13A is a bottom view and FIG. 13B is a perspective view seen from a bottom side.

FIG. 14A is a plan view and FIG. 14B is a back view.

FIG. 15A is a bottom view and FIG. 15B is a perspective view seen from a bottom side.

FIGS. 16A and 16B are views illustrating the medical connector coupling assisting tool illustrated in FIGS. 15A and 15B mounted on three medical connectors having the same configuration as the medical connectors illustrated in FIG. 1, where FIG. 16A is a plan view and FIG. 16B is a back view.

FIG. 17A is a bottom view and FIG. 17B is a perspective view seen from a bottom side.

FIG. 18A is a plan view and FIG. 18B is a back view.

FIG. 19A is a bottom view and FIG. 19B is a perspective view seen from a bottom side.

FIGS. 20A and 20B are views illustrating the medical connector coupling assisting tool illustrated in FIGS. 19A and 19B mounted on the two medical connectors illustrated in FIG. 1, where FIG. 20A is a plan view and FIG. 20B is a back view.

FIG. 21A illustrates a vertical holding state and FIG. 21B illustrates a horizontal holding state.

FIG. 22A is a front view and FIG. 22B is a forward perspective view.

FIGS. 23A and 23B are views illustrating the medical connector coupling assisting tool illustrated in FIGS. 22A and 22B mounted on the two medical connectors illustrated in FIG. 1, where FIG. 23A is a front view and FIG. 23B is a plan view.

FIG. 24A is a bottom view and FIG. 24B is a perspective view seen from a bottom side.

FIGS. 25A and 25B are views illustrating the medical connector coupling assisting tool illustrated in FIGS. 24A and 24B mounted on the two medical connectors illustrated in FIG. 1, where FIG. 25A is a plan view and FIG. 25B is a back view.

DETAILED DESCRIPTION

Figure 1:
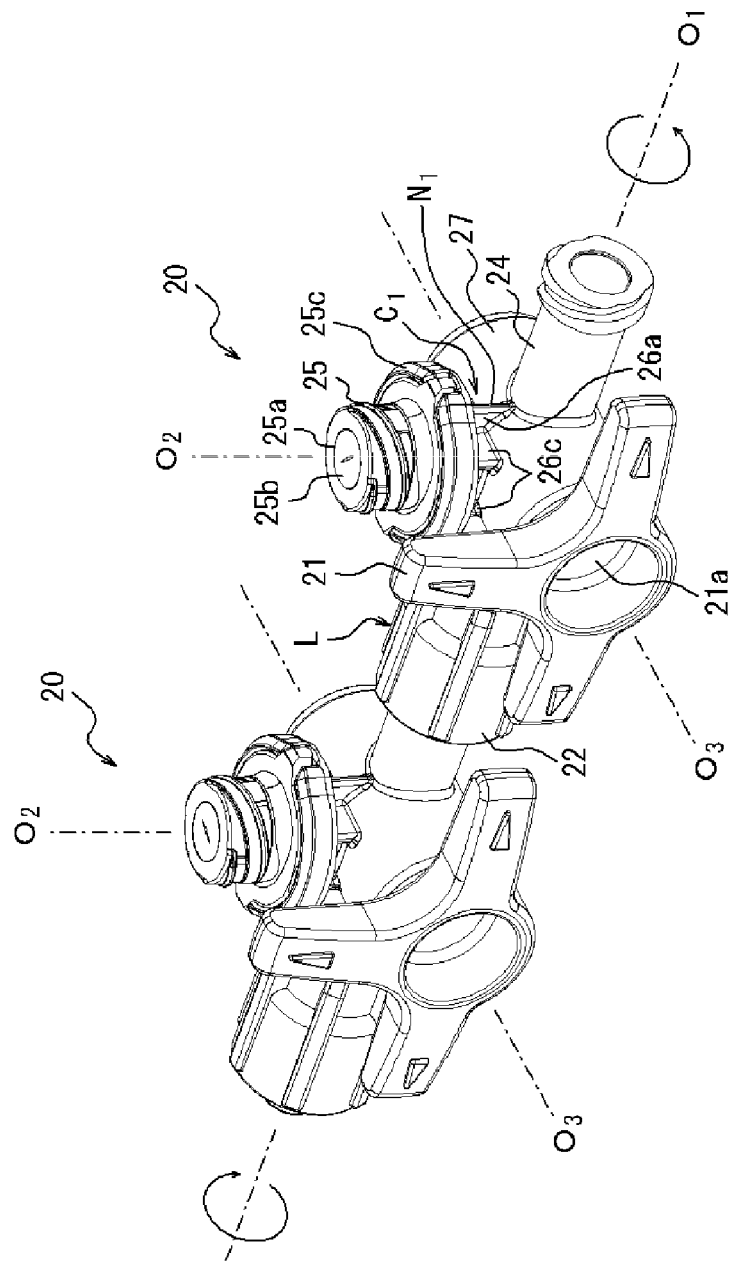
FIG. 1 is a forward perspective view of two medical connectors in an interconnected state on which a medical connector coupling assisting tool according to an embodiment of the present invention is mounted.
Figure 2:
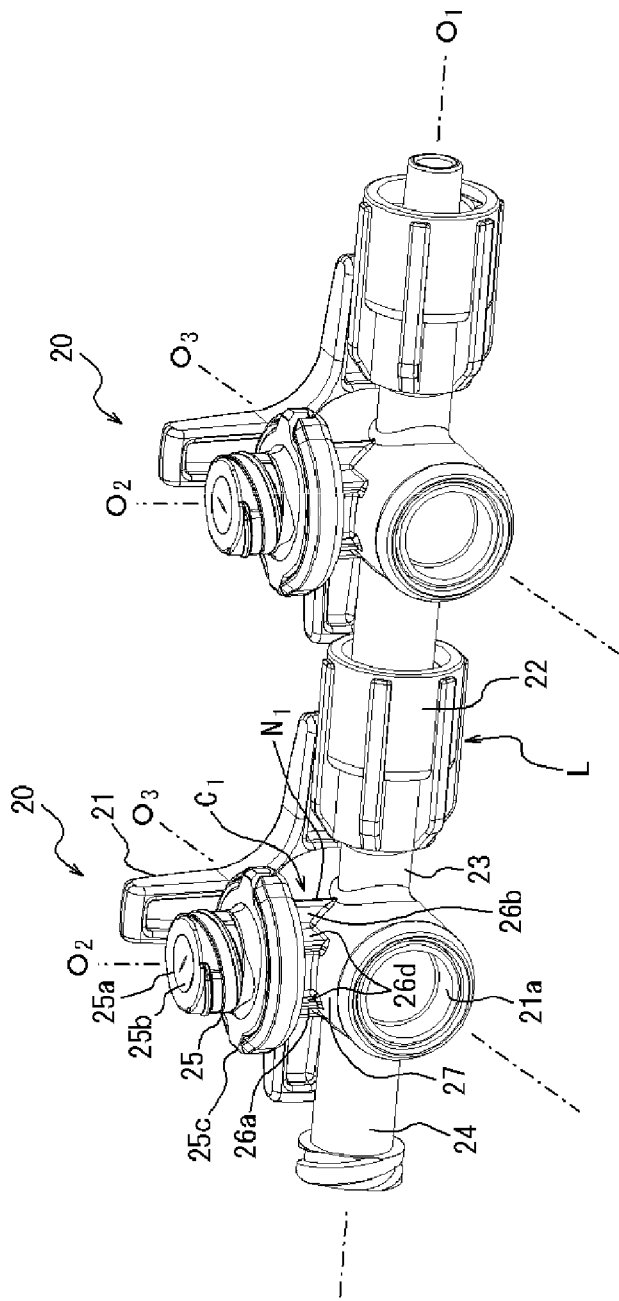
FIG. 2 is a backward perspective view of the two medical connectors illustrated in FIG. 1.
Figure 3:
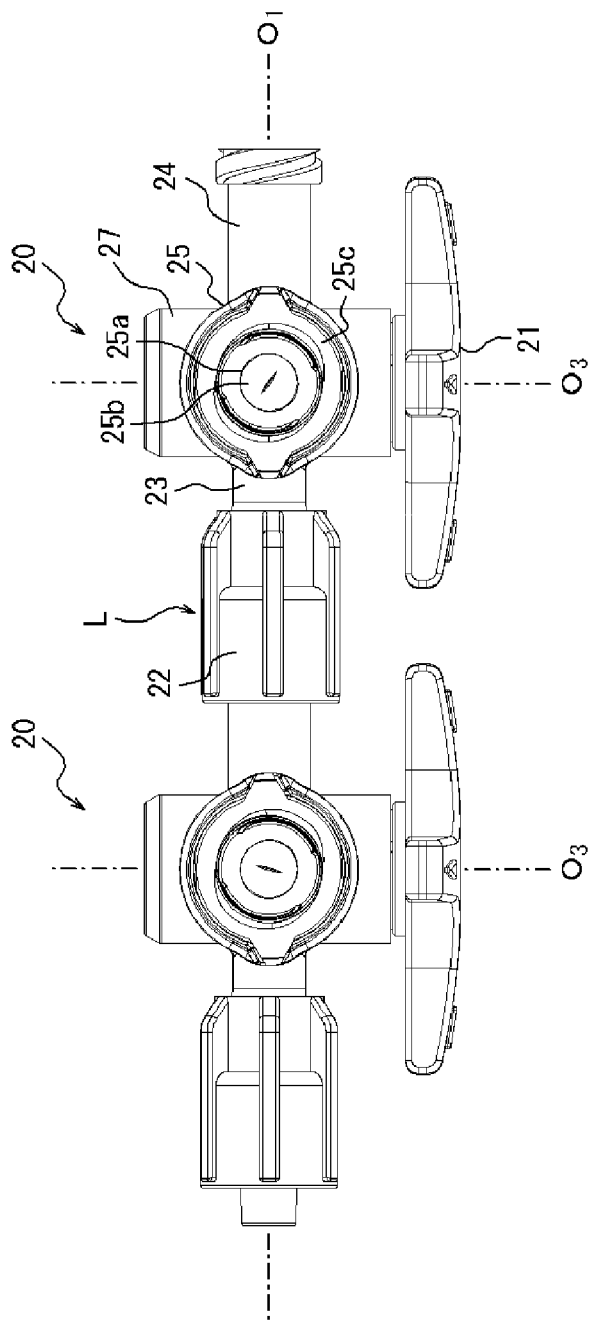
FIG. 3 is a plan view of the two medical connectors illustrated in FIG. 1.
Figure 4:
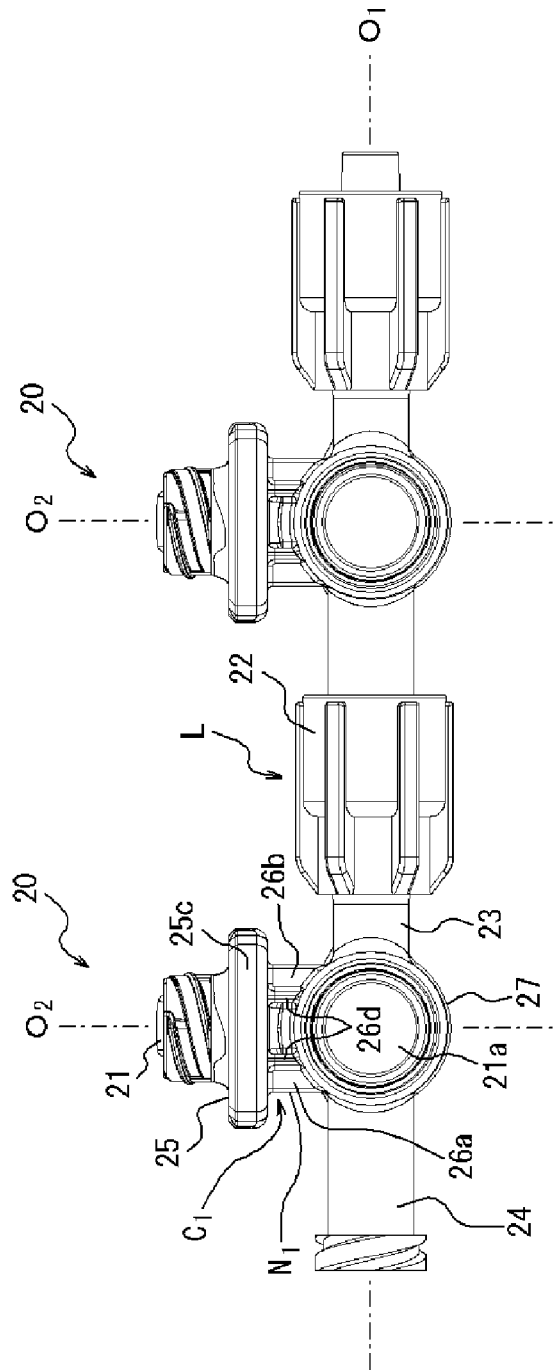
FIG. 4 is a back view of the two medical connectors illustrated in FIG. 1.
Figure 5A:
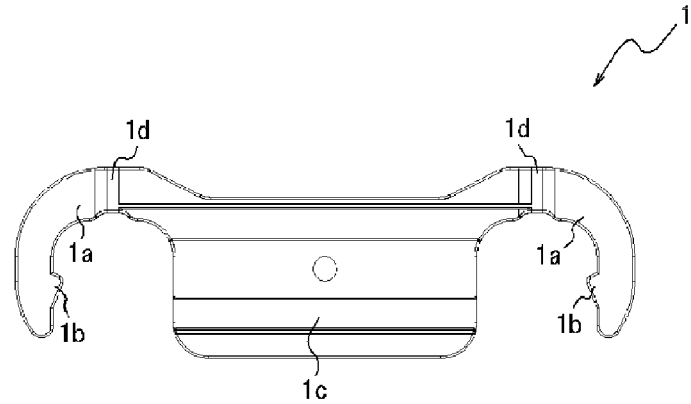
FIGS. 5A and 5B are views illustrating the medical connector coupling assisting tool according to an embodiment of the present invention, where
Figure 5B:
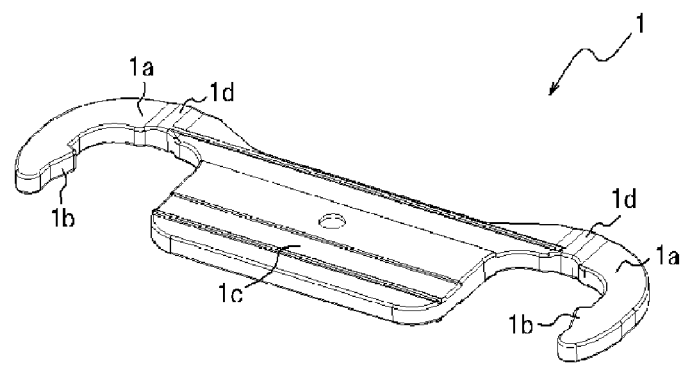

First, a medical connector coupling assisting tool 1 and a medical connector set 100 according to one embodiment of the present invention will be illustrated and described in detail with reference to FIGS. 1 to 6B.

With regard to a medical connector 20 that is used in the present embodiment, a left-right direction means a direction of an axis $O_1$ of a lock connector part L, an upper side means a side on which a mixed injection port 25 is located with respect to the axis $O_1$, a lower side means a side opposite the upper side, a front side means a side on which an operation lever 21 is located with respect to the axis $O_1$, and a back side means a side opposite the front side. With regard to the medical connector coupling assisting tool 1 according to the present embodiment, up-down, left-right, and front-back directions respectively coincide with up-down, left-right, and front-back directions of the medical connector 20 relative to the medical connector coupling assisting tool 1 mounted on the medical connector 20.

The medical connector coupling assisting tool 1 (refer to FIGS. 5A to 6B) according to the present embodiment is used as necessary to suppress looseness of the lock connector part L interconnecting the two medical connectors 20 illustrated in FIGS. 1 to 4. The medical connector set 100 according to the present embodiment includes the two medical connectors 20 and the medical connector coupling assisting tool 1.

As illustrated in FIGS. 1 to 4, in the present embodiment, the medical connector 20 is configured as a three-way cock capable of switching a channel by means of the operation lever 21. The medical connector 20 has a luer lock male connector part 23 and a luer lock female connector part 24. A cylindrical body 22 having a female screw is fit with and held by the male connector part 23 so as to be capable of turning and incapable of slipping off. The female connector part 24 has a male screw with which the cylindrical body 22 can be screwed. The male connector part 23 and the female connector part 24 have a common center axis $O_1$ extending in the left-right direction. The lock connector part L that interconnects the two medical connectors 20 includes the male connector part 23 of the one medical connector 20 and the female connector part 24 of the other medical connector 20 connected to the male connector part 23. In the present embodiment, two medical connectors 20 having the same configuration are used. However, the two medical connectors 20 do not necessarily need to have the same configuration. For example, the cylindrical body 22 can be omitted from the male connector part 23 of the other medical connector 20. Alternatively, the male connector part 23 of the other medical connector 20 may be configured to be joined to a tubular body of another medical tool in advance.

The medical connector 20 includes the mixed injection port 25 having a center axis $O_2$ orthogonal to the center axis $O_1$ of the lock connector part L and extending in the up-down direction. The mixed injection port 25 has a connection opening 25a to which a male connector part of another medical connector (not illustrated) can be connected. A valve body 25b that closes the connection opening 25a is attached to the connection opening 25a. When the male connector part is connected, the valve body 25b is pushed into the connection opening 25a by the male connector part, and a slit formed in the valve body 25b is opened, whereby a channel within the male connector part communicates with a channel within the medical connector 20. In this manner, another medical connector can be coupled to the mixed injection port 25 via the valve body 25b.

The channel within the medical connector 20 is configured to be switched by the operation lever 21 capable of turning around a center axis $O_3$ orthogonal to the center axis $O_1$ of the lock connector part L and extending in the front-back direction. More specifically, when the operation lever 21 is located at a position illustrated in FIGS. 1 to 4, the channels within the male connector part 23, the female connector part 24, and the mixed injection port 25 communicate with one another. In this state, if the operation lever 21 is turned 90° clockwise when seen backward, only the channels within the female connector part 24 and the mixed injection port 25 communicate with each other. When the operation lever 21 is turned 90° in an opposite direction, only the channels within the male connector part 23 and the mixed injection port 25 communicate with each other. Furthermore, in the state illustrated in FIGS. 1 to 4, when the operation lever 21 is turned 180°, only the channels within the male connector part 23 and the female connector part 24 communicate with each other. If the operation lever 21 is turned, from the position illustrated in FIG. 1 to 4, 45°, 135°, 225°, or 315° clockwise when seen backward, all the channels are shut off.

Each of the medical connectors 20 includes a first constriction part $N_1$ that is aligned in parallel with the axis $O_1$ of the lock connector part L in an interconnected state in which the lock connector part L is interposed. The first constriction part $N_1$ is formed at a proximal end part of the mixed injection port 25. Each of the first constriction parts $N_1$ includes the axis $O_2$ orthogonal to the axis $O_1$ of the lock connector part L. A first recessed part $C_1$, that is, a portion defined by the constriction part $N_1$, is provided around the axis $O_2$ of the constriction part $N_1$. In the present embodiment, each of the first constriction parts $N_1$ includes a right side vertical rib 26a projecting to a right side on a right side of an outer peripheral surface of the constriction part $N_1$, a left side vertical rib 26b projecting to a left side on a left side of the outer peripheral surface of the constriction part $N_1$, a pair of front side vertical ribs 26c projecting to a front side on a front side of the outer peripheral surface of the constriction part $N_1$, and a pair of back side vertical ribs 26d projecting to a back side on a back side of the outer peripheral surface of the constriction part $N_1$.

An upper end of the first constriction part $N_1$ is formed by a flange part 25c of the mixed injection port 25. A lower end of the first constriction part $N_1$ is formed by an upper surface of a cylinder part 27 that couples the male connector part 23 to the female connector part 24. An inside wall part 21a formed integrally with the operation lever 21 is fit into the cylinder part 27 so as to be capable of turning around the axis $O_3$. The channel that can be switched by the above-mentioned operation lever 21 is formed between the cylinder part 27 and the inside wall part 21a.

As illustrated in FIGS. 5A to 6B, the medical connector coupling assisting tool 1 includes a plate member having cutout parts defining respective insertion parts 1a. The two insertion parts 1a are U-shaped in plan view. The two insertion parts 1a are configured to be inserted into the respective recessed parts $C_1$ defined by the above-mentioned first constriction parts $N_1$, whereby the two insertion parts 1a are detachably mounted on the constriction parts $N_1$. Each of the insertion parts 1a has a claw part 1b that detachably locks the insertion part 1a to the first constriction part $N_1$. The medical connector coupling assisting tool 1 has a coupling part 1c formed integrally with the two insertion parts 1a to couple the insertion parts 1a together. The medical connector coupling assisting tool 1 is integrally formed preferably by means of injection molding using resin.

The two medical connectors 20 are connected to each other so that each of the first constriction parts $N_1$ is aligned in parallel with the axis $O_1$ of the lock connector part L. Then, the medical connector coupling assisting tool 1 is configured to be attached from behind, with the lock connector part L fastened. In the present embodiment, when the two insertion parts 1a are inserted into the respective recessed parts $C_1$ defined by the first constriction parts $N_1$, the respective claw parts 1b climb over the vertical ribs 26a, 26b facing each other via the axiss $O_2$ of the two first constriction parts $N_1$, and are held by the vertical ribs 26a, 26b so as not to fall off. At this time, since the pair of back side vertical ribs 26d abut the insertion part 1a, movement of the insertion part 1a in the front-back direction can be regulated. A thick part 1d is formed on each of the insertion parts 1a. When the medical connector coupling assisting tool 1 is mounted, as illustrated in FIG. 6B, a front side portion of the thick part 1d is fit into each of the first constriction parts $N_1$ so as not to form a gap in the up-down direction.

Figure 6A:
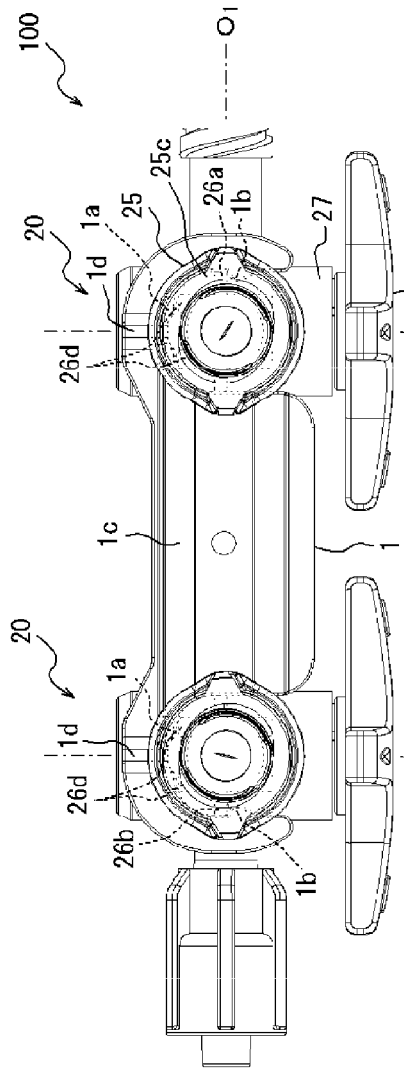
FIGS. 6A and 6B are views illustrating the medical connector coupling assisting tool illustrated in FIGS. 5A and 5B mounted on the two medical connectors illustrated in FIG. 1, where
Figure 6B:
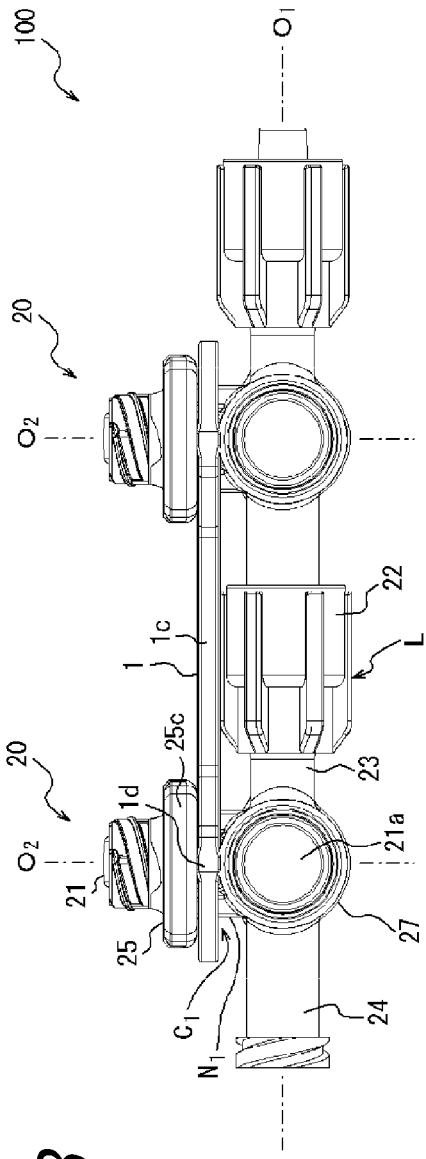
Figure 7A:
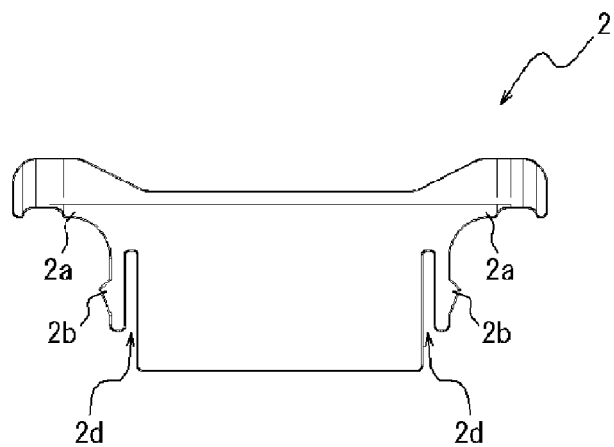
FIGS. 7A and 7B are views illustrating a variation of the medical connector coupling assisting tool according to an embodiment of the present invention, where
Figure 7B:
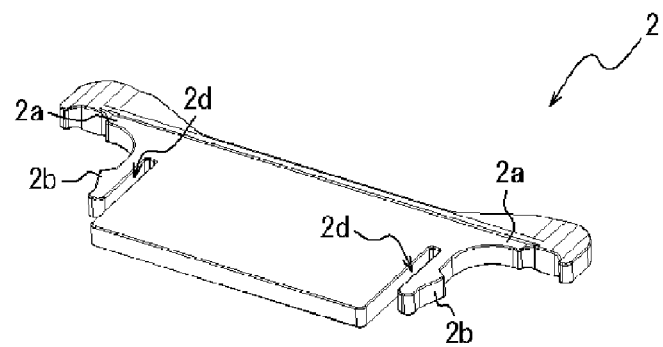
Figure 9A:
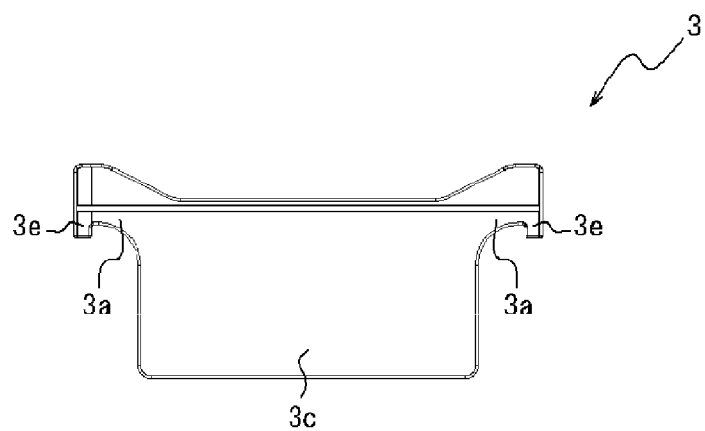
FIGS. 9A and 9B are views illustrating another variation of the medical connector coupling assisting tool according to an embodiment of the present invention, where
Figure 9B:
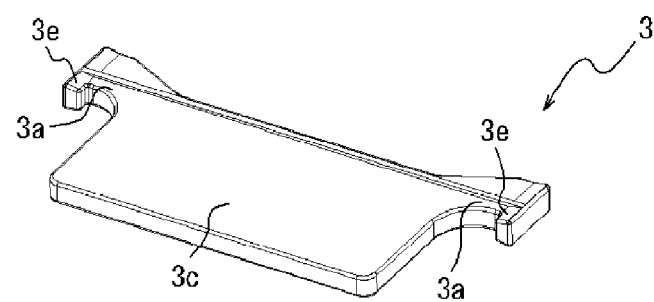
Figure 11A:
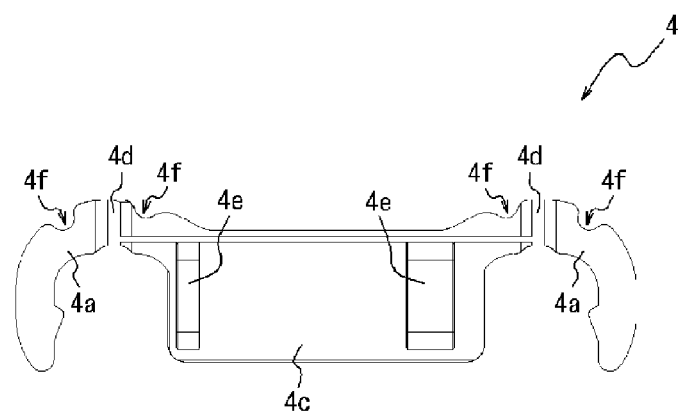
FIGS. 11A and 11B are views illustrating still another variation of the medical connector coupling assisting tool according to an embodiment of the present invention, where
Figure 11B:
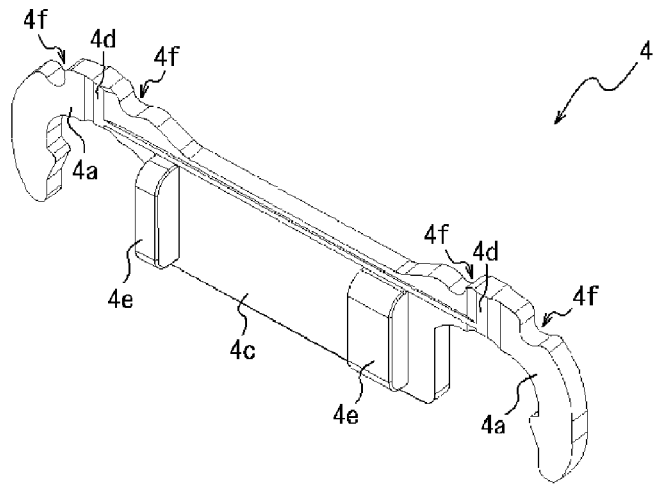
Figures 12A, 12B:
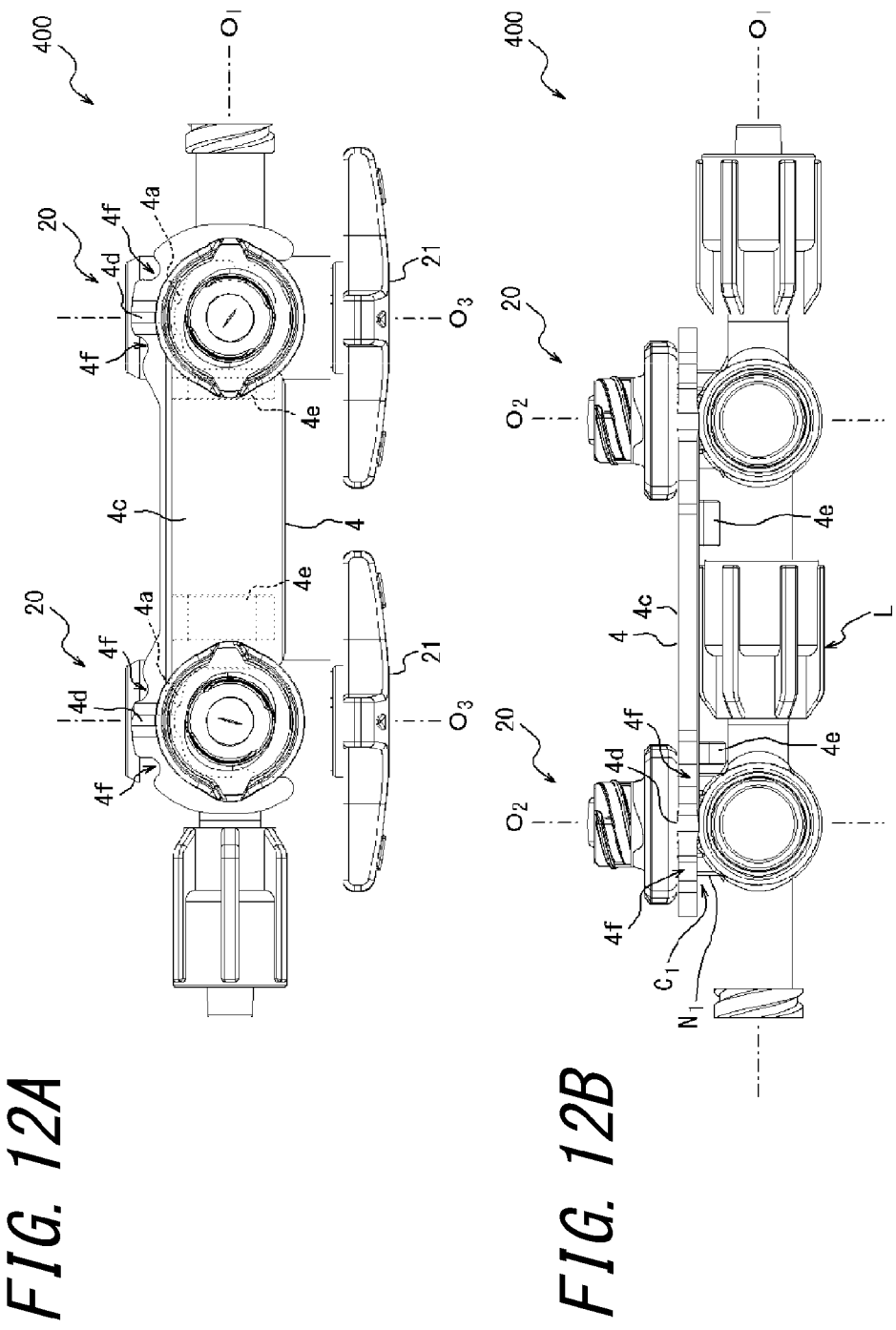
FIGS. 12A and 12B are views illustrating the medical connector coupling assisting tool illustrated in FIGS. 11A and 11B mounted on the two medical connectors illustrated in FIG. 1, where
Figure 13A:
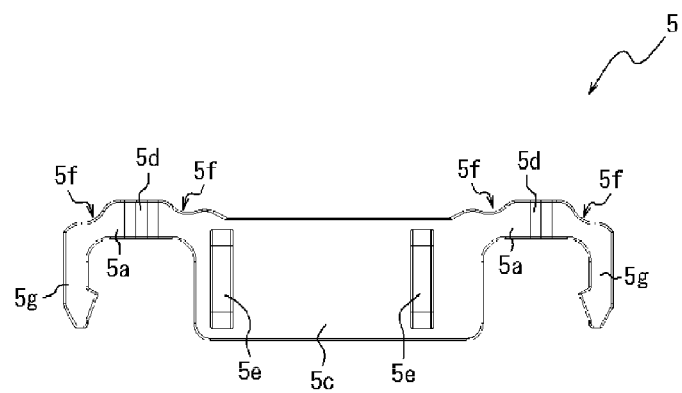
FIGS. 13A and 13B are views illustrating still another variation of the medical connector coupling assisting tool according to an embodiment of the present invention, where
Figure 13B:
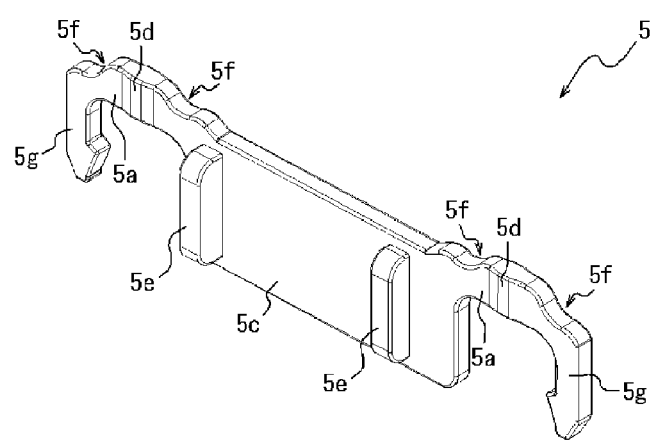
Figures 14A, 14B:
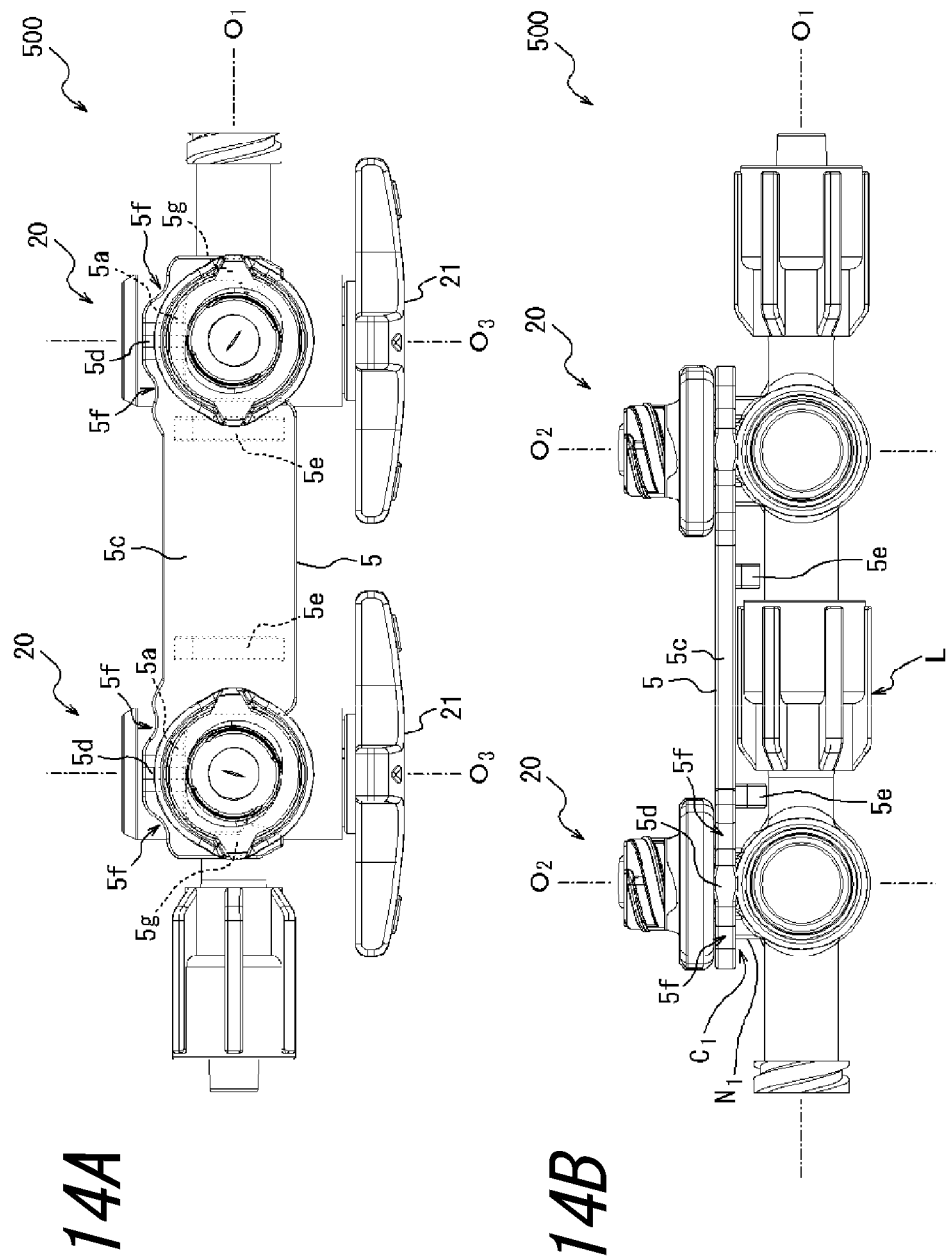
FIGS. 14A and 14B are views illustrating the medical connector coupling assisting tool illustrated in FIGS. 13A and 13B mounted on the two medical connectors illustrated in FIG. 1, where
Figure 15A:
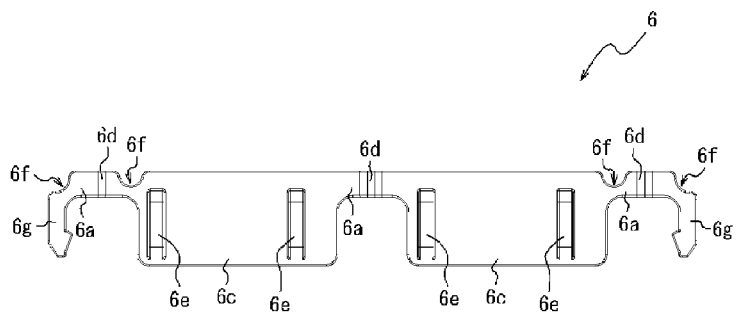
FIGS. 15A and 15B are views illustrating still another variation of the medical connector coupling assisting tool according to an embodiment of the present invention, where
Figure 15B:
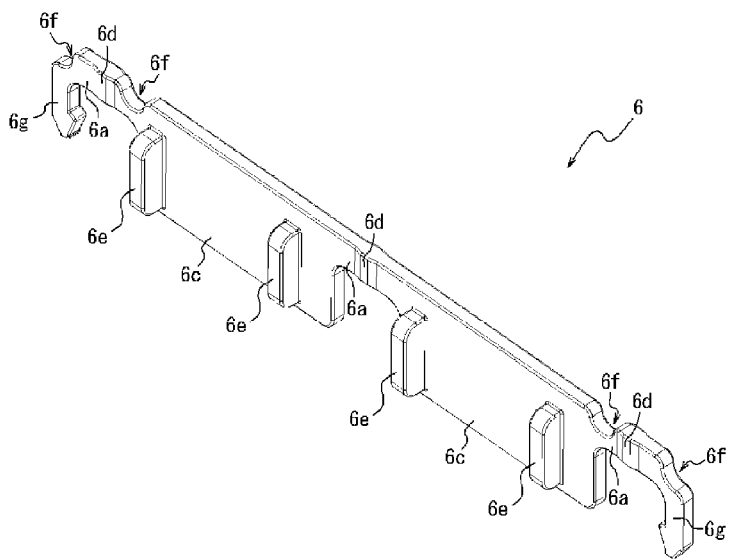
Figure 17A:
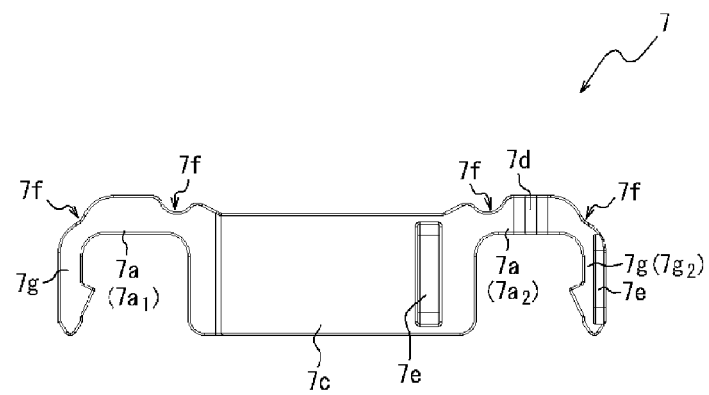
FIGS. 17A and 17B are views illustrating still another variation of the medical connector coupling assisting tool according to an embodiment of the present invention, where
Figure 17B:
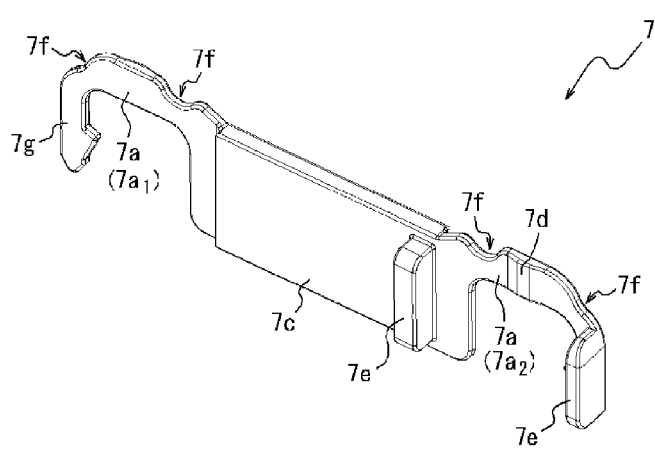
Figure 18A:
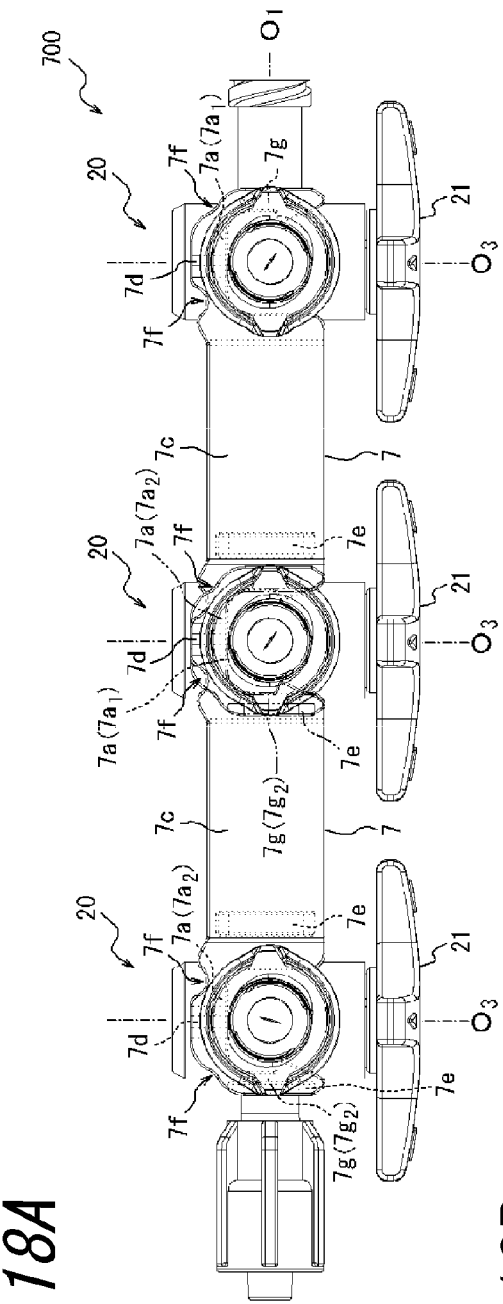
FIGS. 18A and 18B are views illustrating two medical connector coupling assisting tools having the same configuration as the medical connector coupling assisting tool illustrated in FIGS. 17A and 17B mounted on three medical connectors having the same configuration as the medical connectors illustrated in FIG. 1, where
Figure 18B:
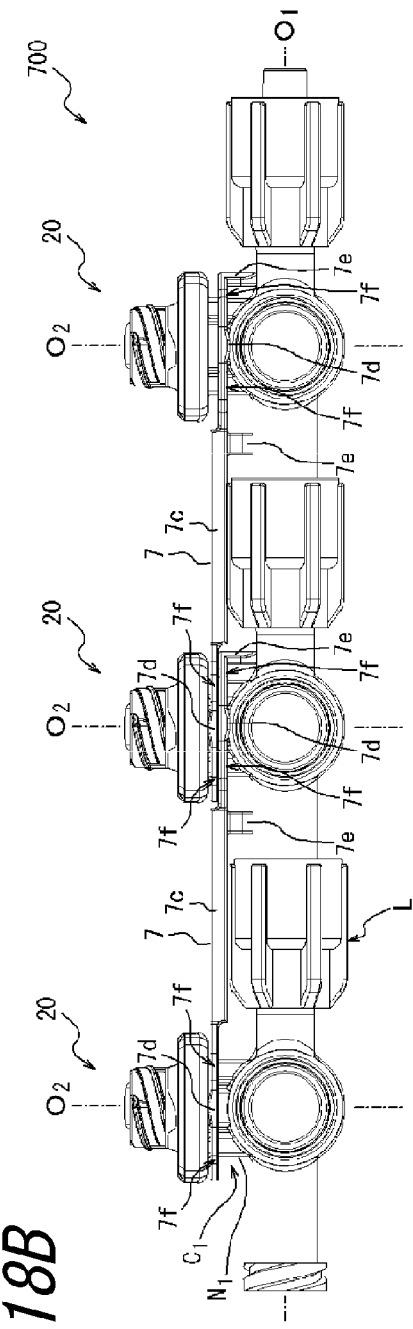
Figure 19A:
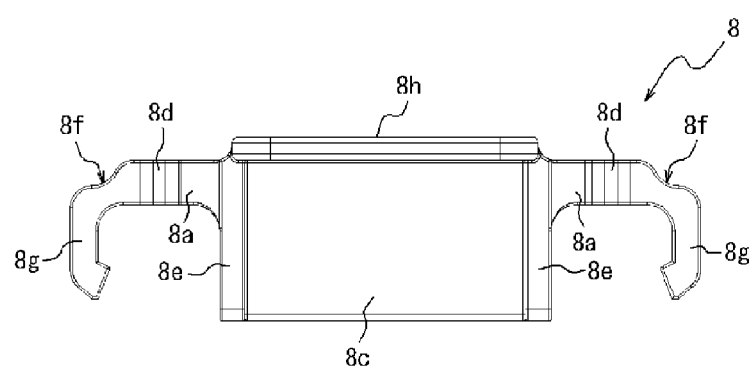
FIGS. 19A and 19B are views illustrating still another variation of the medical connector coupling assisting tool according to an embodiment of the present invention, where
Figure 19B:
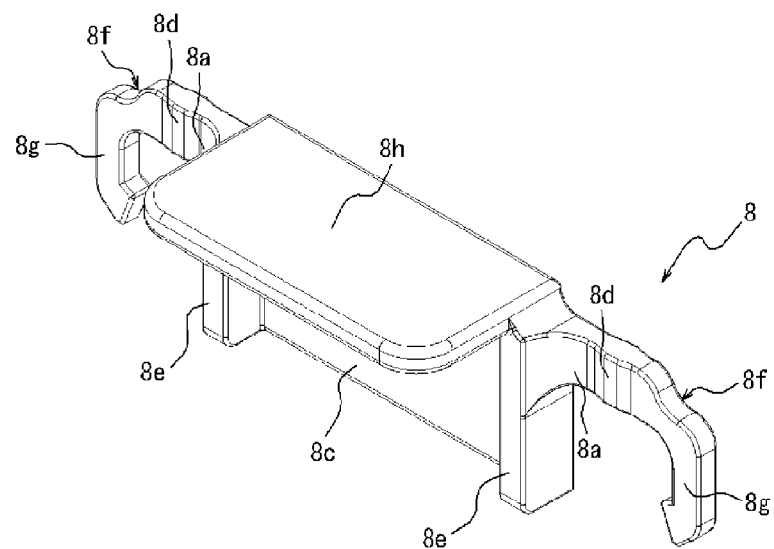

According to the medical connector coupling assisting tool 1 and the medical connector set 100 having the above-mentioned configuration, as illustrated in FIGS. 6A and 6B, while the two medical connectors 20 are interconnected by the lock connector part L, the two insertion parts 1a of the medical connector coupling assisting tool 1 are inserted into the respective recessed parts $C_1$ defined by the first constriction parts $N_1$ of the medical connectors 20. Consequently, the looseness of the lock connector part L can be suppressed by the insertion parts 1a mounted on the respective first constriction parts $N_1$ and the coupling part 1c coupling the insertion parts 1a together. Specifically, when force in a torsion direction around the axis $O_1$ is applied between the two medical connectors 20 in the interconnected state as represented by an arrow in FIG. 1, the two insertion parts 1a mounted on the respective medical connectors 20 are engaged with the first constriction parts $N_1$, whereby rotation between the medical connectors 20 in the torsion direction can be regulated. Since the two insertion parts 1a and the coupling part 1c are integrally formed, the conventional coupling in which plate members are fit with each other is not necessary. Therefore, required dimensional accuracy can be relaxed.

In the present embodiment, as illustrated in FIG. 6A, each of the first constriction parts $N_1$ includes the axis $O_2$ orthogonal to the axis $O_1$ of the lock connector part L, and the recessed part $C_1$ defined by the constriction part $N_1$ is provided around the axis $O_2$ of the constriction part $N_1$. Each of the insertion parts 1a is arranged across the axis $O_1$ of the lock connector part L when seen along the axis $O_2$ of the first constriction part $N_1$ in a mounted state on the first constriction part $N_1$. Therefore, reaction force can be effectively exerted against the above-mentioned force between the medical connectors 20 in the torsion direction, and the looseness of the lock connector part L can be suppressed more reliably.

Next, a variation of the above-mentioned embodiment will be illustrated and described in detail with reference to FIGS. 7A to 8B.

A medical connector coupling assisting tool 2 and a medical connector set 200 according to the present variation have the same configuration as the embodiment mentioned above using FIGS. 1 to 6B except that the medical connector coupling assisting tool 2 has a different shape.

Specifically, in the above-mentioned embodiment, the claw parts 1b are provided at a position where the claw parts 1b face each other via the two first constriction parts $N_1$ when the medical connector coupling assisting tool 1 is mounted. In the present variation, however, claw parts 2b are provided at a position where the claw parts 2b are sandwiched between the two first constriction parts $N_1$ when the medical connector coupling assisting tool 2 is mounted. In addition, in the above-mentioned embodiment, the two insertion parts 1a extend to a position where the insertion parts 1a face each other via the two first constriction parts $N_1$ when the medical connector coupling assisting tool 1 is mounted. In the present variation, however, two insertion parts 2a have their ends on a back side of the two first constriction parts $N_1$ when the medical connector coupling assisting tool 2 is mounted. The claw parts 2b have cutouts 2d for allowing the claw parts 2b to smoothly climb over the vertical ribs 26a, 26b sandwiched between the axis $O_2$ of the two first constriction parts $N_1$ when the medical connector coupling assisting tool 2 is mounted.

According to the medical connector coupling assisting tool 2 and the medical connector set 200 having the above-mentioned configuration, an effect similar to that of the embodiment mentioned above using FIGS. 1 to 6B can be obtained, and a material for constituting the medical connector coupling assisting tool 2 can be reduced.

Next, another variation of the above-mentioned embodiment will be illustrated and described in detail with reference to FIGS. 9A to 10B.

A medical connector coupling assisting tool 3 and a medical connector set 300 according to the present variation have the same configuration as the embodiment mentioned above using FIGS. 1 to 6B except that the medical connector coupling assisting tool 3 has a different shape.

Specifically, in the embodiment mentioned above using FIGS. 1 to 6B, the claw parts 1b that climb over the vertical ribs 26a, 26b to be held so as not to fall off are provided. In the present variation, however, the claw parts 1b are not provided. Instead, in the present variation, each of two insertion parts 3a is formed in a substantially L shape, and a distal end of each of the insertion parts 3a is provided with a projection 3e projecting forward. The distal end of the insertion part 3a and the projection 3e are formed as a thick part. When the medical connector coupling assisting tool 3 is mounted, as illustrated in FIG. 10B, a front side portion of the thick part is fit into each of the first constriction parts $N_1$ so as not to form a gap in the up-down direction. At this time, each of the two projections 3e is inserted between the pair of back side vertical ribs 26d as illustrated in FIG. 10A, whereby engagement holding force between the medical connector coupling assisting tool 3 and the first constriction part $N_1$ is enhanced.

When the medical connector coupling assisting tool 3 is mounted, each of the insertion parts 3a has its end in the center of the pair of back side vertical ribs 26d in the left-right direction or on a side close to the lock connector part L beyond the center. Therefore, in a case where a third medical connector 20 (not illustrated) is further connected to either of the two medical connectors 20 on the axis $O_1$, another medical connector coupling assisting tool 3 (not illustrated) is prepared, and the medical connector coupling assisting tool 3 can be mounted on the newly connected two medical connectors 20 so as to be linked to the above-mentioned medical connector coupling assisting tool 3.

According to the medical connector coupling assisting tool 3 and the medical connector set 300 having the above-mentioned configuration, an effect similar to that of the embodiment mentioned above using FIGS. 1 to 6B can be obtained, and a material for constituting the medical connector coupling assisting tool 3 can be reduced. Three or more medical connectors 20 are available by preparing a plurality of medical connector coupling assisting tools 3.

Next, still another variation of the above-mentioned embodiment will be illustrated and described in detail with reference to FIGS. 11A to 12B.

A medical connector coupling assisting tool 4 and a medical connector set 400 according to the present variation have the same configuration as the embodiment mentioned above using FIGS. 1 to 6B except that the medical connector coupling assisting tool 4 has a different shape.

In the same way as the embodiment mentioned above using FIGS. 1 to 6B, the medical connector coupling assisting tool 4 of the present variation includes a planer plate member having two cutout parts defining respective two insertion parts 4a. The medical connector coupling assisting tool 4 has a coupling part 4c formed integrally with the two insertion parts 4a to couple the insertion parts 4a together.

The medical connector coupling assisting tool 4 is configured such that the coupling part 4c of the plate member is reduced in width in the front-back direction in order to hinder the operation for the operation lever 21 of the medical connector 20 as little as possible. The medical connector coupling assisting tool 4 is also configured such that the plate member has two reinforcing ribs 4e between the above-mentioned cutout parts in order to improve torsional rigidity. Each of the reinforcing ribs 4e extends perpendicular to the axis $O_1$ of the lock connector part L, with the insertion part 4a mounted on each of the first constriction parts $N_1$. In this example, the widths of the two reinforcing ribs 4e in the left-right direction are different. The medical connector coupling assisting tool 4 is further configured such that each of the two insertion parts 4a includes two cuts 4f on both sides across a thick part 4d in order to improve elasticity of the insertion part 4a.

According to the medical connector coupling assisting tool 4 and the medical connector set 400 having the above-mentioned configuration, an effect similar to that of the embodiment mentioned above using FIGS. 1 to 6B can be obtained. Moreover, the operability for the operation lever 21, the torsional rigidity of the plate member, and the elasticity of the insertion part 4a can be improved.

Next, still another variation of the above-mentioned embodiment will be illustrated and described in detail with reference to FIGS. 13A to 14B.

A medical connector coupling assisting tool 5 and a medical connector set 500 according to the present variation have the same configuration as the embodiment mentioned above using FIGS. 1 to 6B except that the medical connector coupling assisting tool 5 has a different shape.

In the same way as the embodiment mentioned above using FIGS. 1 to 6B, the medical connector coupling assisting tool 5 of the present variation includes a planer plate member having two cutout parts defining respective two insertion parts 5a. The medical connector coupling assisting tool 5 has a coupling part 5c formed integrally with the two insertion parts 5a to couple the insertion parts 5a together.

The medical connector coupling assisting tool 5 is configured such that the coupling part 5c of the plate member is reduced in width in the front-back direction in order to hinder the operation for the operation lever 21 of the medical connector 20 as little as possible. The medical connector coupling assisting tool 5 is also configured such that the plate member has two reinforcing ribs 5e between the above-mentioned cutout parts in order to improve the torsional rigidity. Each of the reinforcing ribs 5e extends perpendicular to the axis $O_1$ of the lock connector part L, with the insertion part 5a mounted on each of the first constriction parts $N_1$. In this example, the two reinforcing ribs 5e have the same width in the left-right direction, whereby generation of a sink mark at the time of the injection molding of the plate member is prevented.

The medical connector coupling assisting tool 5 is also configured such that each of the two insertion parts 5a includes two cuts 5f on both sides across a thick part 5d in order to improve the elasticity of the insertion part 5a. Furthermore, in this example, in order to make the medical connector coupling assisting tool 5 less likely to fall off the medical connector 20, distal end regions (regions sandwiching the two cutout parts) 5g of the respective two insertion parts 5a are reduced in width in the left-right direction, so that a portion of the distal end region 5g exposed from the first constriction part $N_1$ becomes smaller in the mounted state of the medical connector coupling assisting tool 5 when seen along the axis $O_2$ of the first constriction part $N_1$.

According to the medical connector coupling assisting tool 5 and the medical connector set 500 having the above-mentioned configuration, an effect similar to that of the embodiment mentioned above using FIGS. 1 to 6B can be obtained. Moreover, the operability for the operation lever 21, the torsional rigidity of the plate member, and the elasticity of the insertion part 5a can be improved, and the generation of the sink mark at the time of the injection molding of the plate member can be prevented. Furthermore, the medical connector coupling assisting tool 5 can be made less likely to fall off the medical connector 20.

Next, still another variation of the above-mentioned embodiment will be illustrated and described in detail with reference to FIGS. 15A to 16B.

A medical connector coupling assisting tool 6 and a medical connector set 600 according to the present variation have the same configuration as the embodiment mentioned above using FIGS. 1 to 6B except that the medical connector coupling assisting tool 6 including three insertion parts 6a is used, and that the medical connector set 600 includes three medical connectors 20.

The medical connector coupling assisting tool 6 of the present variation includes a planer plate member having three cutout parts defining the respective three insertion parts 6a. The medical connector coupling assisting tool 5 has two coupling parts 6c formed integrally with the three insertion parts 6a to couple the insertion parts 6a together.

The medical connector coupling assisting tool 6 is configured such that the coupling part 6c of the plate member is reduced in width in the front-back direction in order to hinder the operation for the operation lever 21 of the medical connector 20 as little as possible. The medical connector coupling assisting tool 6 is also configured such that the plate member has two reinforcing ribs 6e between the above-mentioned cutout parts in order to improve the torsional rigidity. Each of the reinforcing ribs 6e extends perpendicular to the axis $O_1$ of the lock connector part L, with the three insertion parts 6a mounted on the respective first constriction parts $N_1$. In this example, the two reinforcing ribs 6e have the same width in the left-right direction, whereby the generation of the sink mark at the time of the injection molding of the plate member is prevented.

The medical connector coupling assisting tool 6 is also configured such that each of the two insertion parts 6a located at both end parts in the left-right direction includes two cuts 6f on both sides across a thick part 6d in order to improve the elasticity of the insertion part 6a. Furthermore, in this example, in order to make the medical connector coupling assisting tool 6 less likely to fall off the medical connector 20, distal end regions (regions sandwiching the two cutout parts) 6g of the respective two insertion parts 6a located at both end parts in the left-right direction are reduced in width in the left-right direction, so that a portion of the distal end region 6g exposed from the first constriction part $N_1$ becomes smaller in the mounted state of the medical connector coupling assisting tool 6 when seen along the axis $O_2$ of the first constriction part $N_1$.

According to the medical connector coupling assisting tool 6 and the medical connector set 600 having the above-mentioned configuration, an effect similar to that of the embodiment mentioned above using FIGS. 1 to 6B can be obtained when the three medical connectors 20 are interconnected. Moreover, the operability for the operation lever 21, the torsional rigidity of the plate member, and the elasticity of the insertion part 6a can be improved, and the generation of the sink mark at the time of the injection molding of the plate member can be prevented. Furthermore, the medical connector coupling assisting tool 6 can be made less likely to fall off the medical connector 20.

Next, still another variation of the above-mentioned embodiment will be illustrated and described in detail with reference to FIGS. 17A to 18B.

A medical connector coupling assisting tool 7 and a medical connector set 700 according to the present variation have the same configuration as the embodiment mentioned above using FIGS. 1 to 6B except that the medical connector set 700 includes two medical connector coupling assisting tools 7 and three medical connectors 20, and that the medical connector coupling assisting tool 7 has a different shape.

In the same way as the embodiment mentioned above using FIGS. 1 to 6B, each of the medical connector coupling assisting tools 7 of the present variation includes a planer plate member having two cutout parts defining respective two insertion parts 7a. Each of the medical connector coupling assisting tools 7 has a coupling part 7c formed integrally with the two insertion parts 7a to couple the insertion parts 7a together.

The medical connector coupling assisting tool 7 is configured such that one $7a_1$ of the two insertion parts 7a of the plate member can be attached to or detached from the first constriction part $N_1$ on which the other $7a_2$ of the two insertion parts 7a of another plate member having the same configuration has been mounted. Specifically, the one $7a_1$ and the other $7a_2$ of the two insertion parts 7a are reduced in width in the up-down direction as compared with the width of the coupling part 7c in the up-down direction. More specifically, the width of each of the one $7a_1$ and the other $7a_2$ of the two insertion parts 7a in the up-down direction is reduced to approximately half the width of the coupling part 7c in the up-down direction. The medical connector coupling assisting tool 7 is also configured such that the one $7a_1$ and the other $7a_2$ of the two insertion parts 7a of the plate member are provided on different levels so that the two plate members have a flush shape when the two plate members are continuously mounted on the medical connectors 20.

The medical connector coupling assisting tool 7 is also configured such that the coupling part 7c of the plate member is reduced in width in the front-back direction in order to hinder the operation for the operation lever 21 of the medical connector 20 as little as possible. The medical connector coupling assisting tool 7 is also configured such that the plate member has a single reinforcing rib 7e between the above-mentioned cutout parts, and a distal end region $7g_2$ of the other $7a_2$ of the two insertion parts 7a also has a single reinforcing rib 7e in order to improve the torsional rigidity. Each of the reinforcing ribs 7e extends perpendicular to the axis $O_1$ of the lock connector part L, with the insertion part 7a mounted on each of the first constriction parts $N_1$.

The medical connector coupling assisting tool 7 is also configured such that each of the two insertion parts 7a includes two cuts 7f on both sides across a thick part 7d in order to improve the elasticity of the insertion part 7a. Furthermore, in this example, in order to make the medical connector coupling assisting tool 7 less likely to fall off the medical connector 20, distal end regions (regions sandwiching the two cutout parts) 7g of the respective two insertion parts 7a are reduced in width in the left-right direction, so that a portion of the distal end region 7g exposed from the first constriction part $N_1$ becomes smaller in the mounted state of the medical connector coupling assisting tool 7 when seen along the axis $O_2$ of the first constriction part $N_1$.

According to the medical connector coupling assisting tool 7 and the medical connector set 700 having the above-mentioned configuration, an effect similar to that of the embodiment mentioned above using FIGS. 1 to 6B can be obtained. In addition, the three medical connectors 20 can be interconnected as necessary, and the interconnected state can be successfully held using the two medical connector coupling assisting tools 7. By using an additional medical connector 20 and an additional medical connector coupling assisting tool 7, four or more medical connectors 20 can be interconnected. According to the medical connector coupling assisting tool 7 and the medical connector set 700, the operability for the operation lever 21, the torsional rigidity of the plate member, and the elasticity of the insertion part 7a can be improved, and the medical connector coupling assisting tool 7 can be made less likely to fall off the medical connector 20.

Next, still another variation of the above-mentioned embodiment will be illustrated and described in detail with reference to FIGS. 19A to 21B.

A medical connector coupling assisting tool 8 and a medical connector set 800 according to the present variation have the same configuration as the embodiment mentioned above using FIGS. 1 to 6B except that the medical connector coupling assisting tool 8 has a different shape.

In the same way as the embodiment mentioned above using FIGS. 1 to 6B, the medical connector coupling assisting tool 8 of the present variation includes a planer plate member having two cutout parts defining respective two insertion parts 8a. The medical connector coupling assisting tool 8 has a coupling part 8c formed integrally with the two insertion parts 8a to couple the insertion parts 8a together.

The medical connector coupling assisting tool 8 is configured such that the coupling part 8c of the plate member is reduced in forward projection width in order to hinder the operation for the operation lever 21 of the medical connector 20 as little as possible. The medical connector coupling assisting tool 8 is also configured such that the plate member has two reinforcing ribs 8e between the above-mentioned cutout parts in order to improve the torsional rigidity. Each of the reinforcing ribs 8e extends perpendicular to the axis $O_1$ of the lock connector part L, with the insertion part 8a mounted on each of the first constriction parts $N_1$. In this example, the two reinforcing ribs 8e have the same width in the left-right direction, whereby the generation of the sink mark at the time of the injection molding of the plate member is prevented.

The medical connector coupling assisting tool 8 is also configured such that each of the two insertion parts 8a includes a single cut 8f on the outside of a thick part 8d in order to improve the elasticity of the insertion part 8a. Furthermore, in this example, in order to make the medical connector coupling assisting tool 8 less likely to fall off the medical connector 20, distal end regions (regions sandwiching the two cutout parts) 8g of the respective two insertion parts 8a are reduced in width in the left-right direction, so that a portion of the distal end region 8g exposed from the first constriction part $N_1$ becomes smaller in the mounted state of the medical connector coupling assisting tool 8 when seen along the axis $O_2$ of the first constriction part $N_1$.

Moreover, in the present variation, the medical connector coupling assisting tool 8 includes an overhanging part 8h between the cutout parts of the plate member. The overhanging part 8h is arranged along an end edge of the plate member and extends in a direction intersecting (in this example, orthogonal to) the plate member. In this example, the overhanging part 8h is arranged continuously between the cutout parts and connected to the two left and right reinforcing ribs 8e. In this example, the overhanging part 8h is formed in a substantially rectangular plate shape, a distal end edge (lower end edge) of which extends to such a position that the overhanging part 8h covers the lock connector part L while the insertion part 8a is mounted on each of the first constriction parts $N_1$. In this example, the lower end edge of the overhanging part 8h is aligned to be flush with a lower end edge of the cylinder part 27 while the insertion part 8a is mounted on each of the first constriction parts $N_1$. Furthermore, in this example, a front end edge of the overhanging part 8h is aligned to be flush with a front end edge of the cylinder part 27 while the insertion part 8a is mounted on each of the first constriction parts $N_1$.

According to the medical connector coupling assisting tool 8 and the medical connector set 800 having the above-mentioned configuration, an effect similar to that of the embodiment mentioned above using FIGS. 1 to 6B can be obtained. Moreover, the operability for the operation lever 21, the torsional rigidity of the plate member, and the elasticity of the insertion part 8a can be improved, and the generation of the sink mark at the time of the injection molding of the plate member can be prevented. Furthermore, the medical connector coupling assisting tool 8 can be made less likely to fall off the medical connector 20.

Figure 21A:
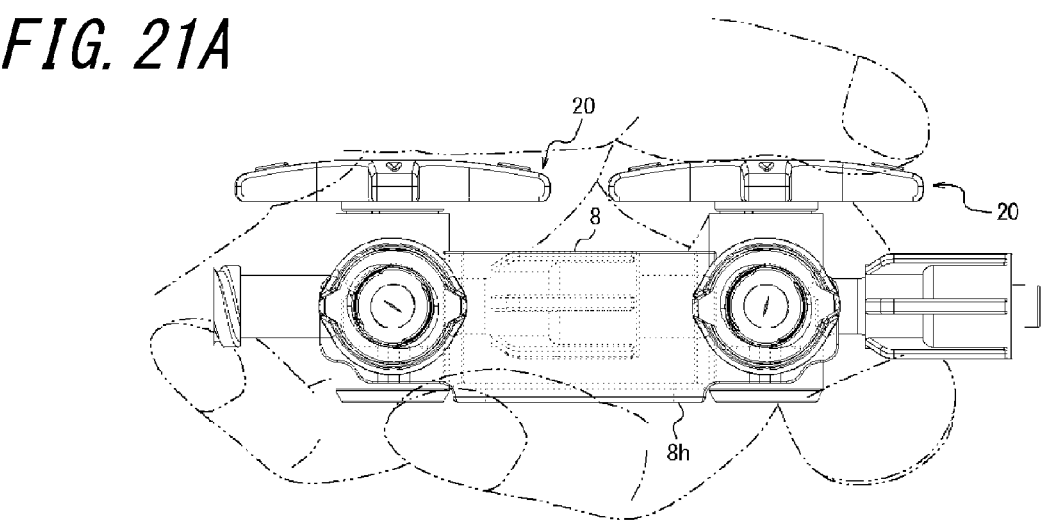
FIGS. 21A and 21B are appearance views illustrating the medical connectors with the medical connector coupling assisting tool illustrated in FIGS. 20A and 20B held by a hand indifferent directions, where
Figure 21B:
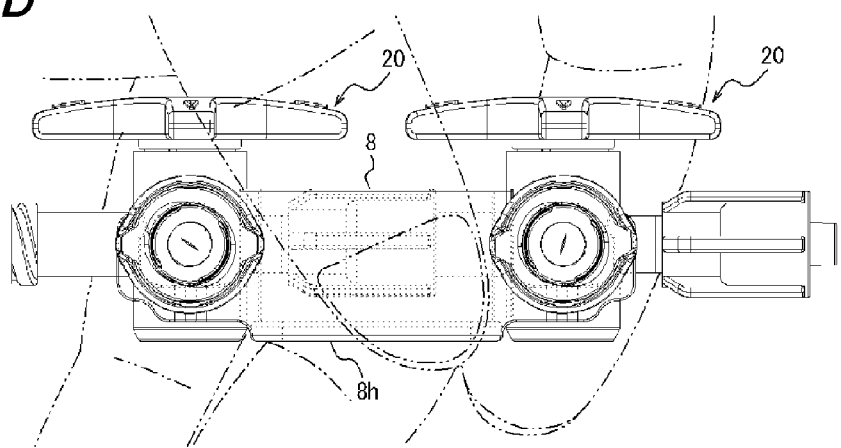
Figure 22A:
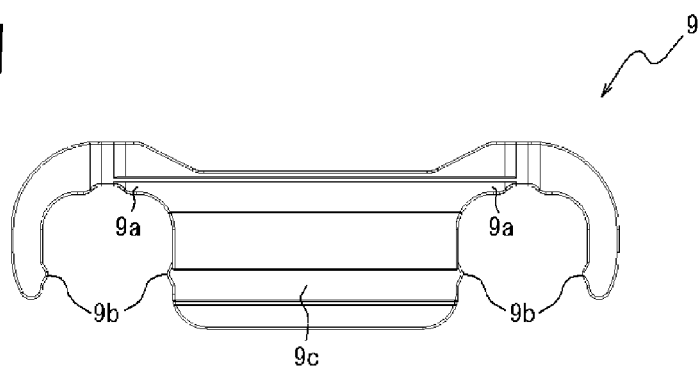
FIGS. 22A and 22B are views illustrating a medical connector coupling assisting tool according to another embodiment of the present invention, where
Figure 22B:
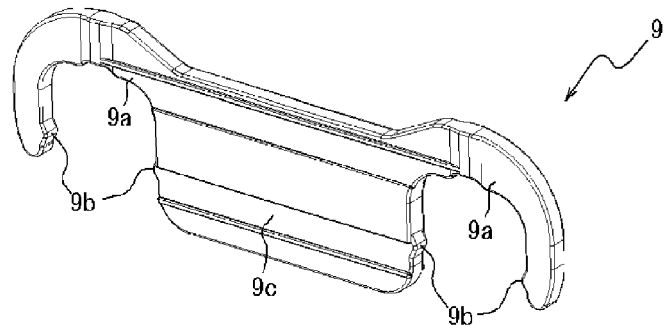
Figure 24A:
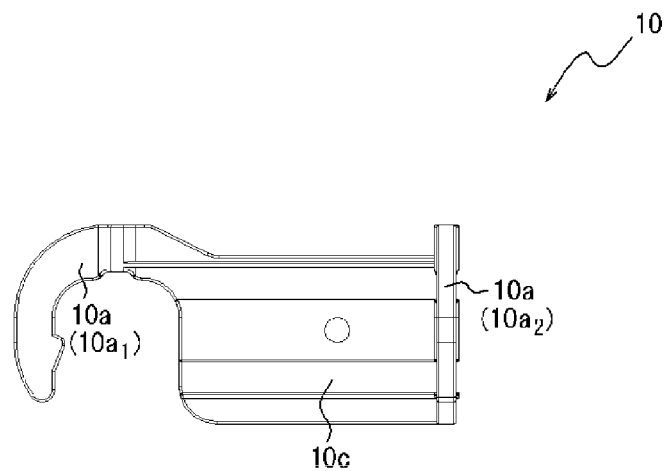
FIGS. 24A and 24B are views illustrating a medical connector coupling assisting tool according to still another embodiment of the present invention, where
Figure 24B:
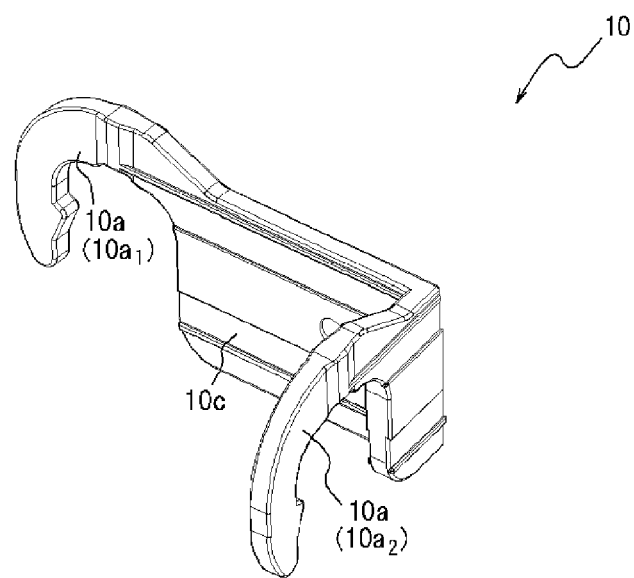

Moreover, the present variation includes, between the cutout parts of the plate member, the overhanging part 8h arranged along the end edge of the plate member and extending in the direction intersecting the plate member. Therefore, the torsional rigidity of the plate member can be further enhanced as compared with a case where only the reinforcing rib 8e is provided. Since the present variation includes the overhanging part 8h, the lock connector part L can be covered with the overhanging part 8h at the time of mounting on the medical connector 20. Therefore, the looseness of the lock connector part L that is generated by unintended contact with the lock connector part L can be suppressed. Since the present variation includes the overhanging part 8h, a difference in level of a grasped part can be reduced by the overhanging part 8h both when the medical connector 20 with the medical connector coupling assisting tool 8 is grasped in a vertical holding state as illustrated in FIG. 21A and when it is grasped in a horizontal holding state as illustrated in FIG. 21B. Consequently, the medical connector 20 with the medical connector coupling assisting tool 8 can be easily held. The overhanging part 8h can also be referred to as a flat plate part arranged along the end edge of the plate member between the cutout parts of the plate member and extending in the direction intersecting the plate member.

Next, a medical connector coupling assisting tool 9 and a medical connector set 900 according to another embodiment of the present invention will be illustrated and described in detail with reference to FIGS. 22A to 23B.

The medical connector coupling assisting tool 9 and the medical connector set 900 according to the present embodiment have the same configuration as the embodiment mentioned above using FIGS. 1 to 6B except that the medical connector coupling assisting tool 9 is mounted at a different position and has a different shape.

Specifically, in the above-mentioned embodiment, the medical connector coupling assisting tool 1 is mounted on the first constriction part $N_1$ formed at the mixed injection port 25. In the present embodiment, however, the medical connector coupling assisting tool 9 is configured to be mounted on a second constriction part $N_2$ formed by the operation lever 21, the cylinder part 27, and the mixed injection port 25.

The medical connector coupling assisting tool 9 includes a plate member having cutout parts defining respective insertion parts 9a. The two insertion parts 9a are U-shaped in plan view. The two insertion parts 9a are configured to be inserted into respective two recessed parts $C_2$ defined by the above-mentioned second constriction parts $N_2$, whereby the two insertion parts 9a are detachably mounted on the constriction parts $N_2$. Each of the insertion parts 9a has a pair of claw parts 9b that detachably locks the insertion part 9a to the second constriction part $N_2$. The medical connector coupling assisting tool 9 has a coupling part 9c formed integrally with the two insertion parts 9a to couple the insertion parts 9a together. The medical connector coupling assisting tool 9 is integrally formed preferably by means of the injection molding using resin.

The two medical connectors 20 are connected to each other so that each of the second constriction parts $N_2$ is aligned in parallel with the axis $O_1$ of the lock connector part L. Then, the medical connector coupling assisting tool 9 is configured to be attached from above, with the lock connector part L fastened. In the present embodiment, when the two insertion parts $9a$ are inserted into the respective recessed parts $C_2$ defined by the second constriction parts $N_2$, the respective pairs of claw parts $9b$ climb over outer peripheral surfaces of the cylinder parts 27, namely, the second constriction parts $N_2$, and are held by the cylinder parts 27 so as not to fall off.

According to the medical connector coupling assisting tool 9 and the medical connector set 900 having the above-mentioned configuration, as illustrated in FIGS. 23A and 23B, while the two medical connectors 20 are interconnected by the lock connector part L, the two insertion parts $9a$ of the medical connector coupling assisting tool 9 are inserted into the respective recessed parts $C_2$ defined by the second constriction parts $N_2$ of the medical connectors 20. Consequently, the looseness of the lock connector part L can be suppressed by the insertion parts $9a$ mounted on the respective second constriction parts $N_2$ and the coupling part $9c$ coupling the insertion parts $9a$ together. Specifically, when the force in the torsion direction around the axis $O_1$ is applied between the two medical connectors 20 in the interconnected state as represented by the arrow in FIG. 1, the two insertion parts $9a$ mounted on the respective medical connectors 20 are engaged with the second constriction parts $N_2$, whereby the rotation between the medical connectors 20 in the torsion direction can be regulated. Since the two insertion parts $9a$ and the coupling part $9c$ are integrally formed, the conventional coupling in which plate members are fit with each other is not necessary. Therefore, the required dimensional accuracy can be relaxed.

In the present embodiment, as illustrated in FIG. 23A, each of the second constriction parts $N_2$ includes the axis $O_3$ orthogonal to the axis $O_1$ of the lock connector part L, and the recessed part $C_2$ defined by the constriction part $N_2$ is provided around the axis $O_3$ of the constriction part $N_2$. Each of the insertion parts $9a$ is arranged across the axis $O_1$ of the lock connector part L when seen along the axis $O_3$ of the second constriction part $N_2$ in a mounted state on the second constriction part $N_2$. Therefore, reaction force can be effectively exerted against the above-mentioned force between the medical connectors 20 in the torsion direction, and the looseness of the lock connector part L can be suppressed more reliably.

Next, a medical connector coupling assisting tool 10 and a medical connector set 1000 according to still another embodiment of the present invention will be illustrated and described in detail with reference to FIGS. 24A to 25B.

The medical connector coupling assisting tool 10 and the medical connector set 1000 according to the present embodiment have the same configuration as the embodiment mentioned above using FIGS. 1 to 6B except that the medical connector coupling assisting tool 10 has a different shape and that a female connector part 24' of the medical connector 20 has a different shape.

In the same way as the embodiment mentioned above using FIGS. 1 to 6B, the medical connector coupling assisting tool 10 of the present embodiment includes a plate member having two cutout parts defining respective two insertion parts $10a$. The medical connector coupling assisting tool 10 has a coupling part $10c$ formed integrally with the two insertion parts $10a$ to couple the insertion parts $10a$ together.

The medical connector coupling assisting tool 10 is configured such that the plate member is bent downward at an angle of about 90° at the coupling part $10c$. In the present embodiment, the medical connector 20 includes the female connector part 24' serving as a third constriction part $N_3$ and the first constriction part $N_1$. In the interconnected state, the female connector part 24' is located in parallel with the axis $O_1$ of the lock connector part L (in other words, has a common axis with the axis $O_1$ of the lock connector part L), and the first constriction part $N_1$ is located perpendicular to the axis $O_1$ (in other words, has an axis perpendicular to the axis $O_1$).

In the present embodiment, while the two medical connectors 20 are interconnected, one insertion part $10a_1$ of the medical connector coupling assisting tool 10 can be inserted into a portion defined by the first constriction part $N_1$ to be detachably mounted on the first constriction part $N_1$, and the other insertion part $10a_2$ located below can be inserted into a portion defined by the third constriction part $N_3$ to be detachably mounted on the third constriction part $N_3$. In the present embodiment, the portion defined by the third constriction part $N_3$ is provided with an uneven part $24a$. When the other insertion part $10a_2$ of the medical connector coupling assisting tool 10 is mounted, the uneven part $24a$ prevents the insertion part $10a_2$ from relatively rotating around the axis $O_1$ with respect to the third constriction part $N_3$.

Therefore, by means of the medical connector coupling assisting tool 10 and the medical connector set 1000 according to the present embodiment, as illustrated in FIGS. 25A and 25B, while the two medical connectors 20 are interconnected by the lock connector part L, the two insertion parts $10a$ of the medical connector coupling assisting tool 10 are inserted into the portion defined by the first constriction part $N_1$ and the portion defined by the third constriction part $N_3$ of the medical connectors 20. Consequently, the looseness of the lock connector part L can be suppressed by the insertion parts $10a$ mounted on the respective first constriction part $N_1$ and third constriction part $N_3$ and the coupling part $10c$ coupling the insertion parts $10a$ together.

Specifically, when the force in the torsion direction around the axis $O_1$ is applied between the two medical connectors 20 in the interconnected state as represented by the arrow in FIG. 1, the two insertion parts $10a$ mounted on the respective medical connectors 20 are engaged with the first constriction part $N_1$ and the third constriction part $N_3$, whereby the rotation between the medical connectors 20 in the torsion direction can be regulated. Since the two insertion parts $10a$ and the coupling part $10c$ are integrally formed, the conventional coupling in which plate members are fit with each other is not necessary. Therefore, the required dimensional accuracy can be relaxed.

The medical connector coupling assisting tool 10 and the medical connector set 1000 according to the present embodiment are configured such that the two insertion parts $10a$ are engaged with the first constriction part $N_1$ and the third constriction part $N_3$. Instead of this configuration, the two insertion parts $10a$ can be configured to be engaged with the second constriction part $N_2$ and the third constriction part $N_3$.

Figure 26:
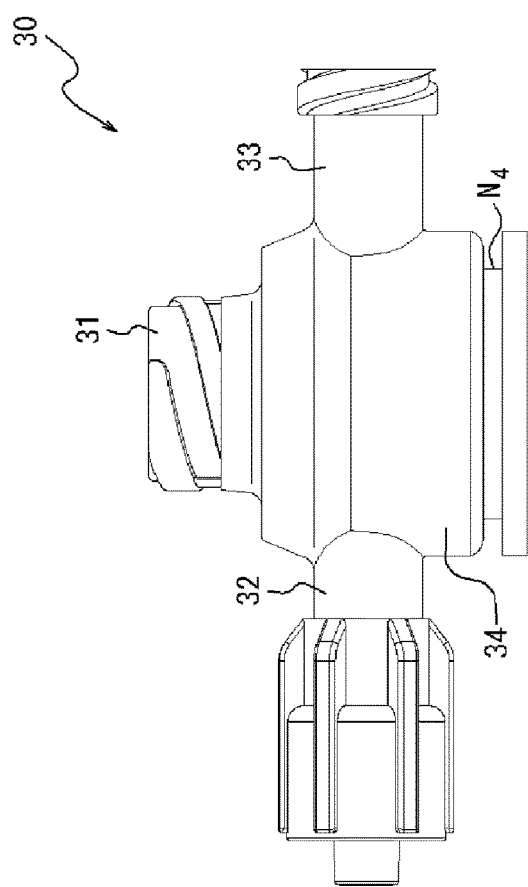
FIG. 26 is a front view illustrating another example of a medical connector on which the medical connector coupling assisting tool according to an embodiment of the present invention can be mounted.

The above-mentioned description only illustrates an embodiment of the present invention, and the scope of the claims can be variously changed. For example, although the medical connector 20 is configured as the three-way cock capable of switching the channel by means of the operation lever 21 in the above description, the medical connector 20 does not necessarily need to be limited to this configuration. As illustrated in FIG. 26, for example, the medical connector 20 can be configured as a T port 30 including a mixed injection port 31, a luer lock male connector part 32, a luer lock female connector part 33, and a barrel part 34 that couples the mixed injection port 31, the male connector part 32, and the female connector part 33. In this case, an end part of the barrel part 34 opposite to the mixed injection port 31 is provided with a constriction part $N_4$ formed by, for example, an annular groove, and the insertion part of the medical connector coupling assisting tool (not illustrated) can be configured to be mounted on the constriction part $N_4$.

In the above-mentioned embodiment, each of the medical connector coupling assisting tools 1 to 5 and 8 to 10 is configured to suppress the looseness of the lock connector part L interconnecting the two medical connectors 20. Alternatively, a single medical connector coupling assisting tool can be configured to be adapted to, for example, three or more medical connectors 20. In this case, the medical connector coupling assisting tool can be provided with three or more insertion parts. Similarly, although the medical connector coupling assisting tool 6 has the three insertion parts, the medical connector coupling assisting tool 6 may be configured to include four or more insertion parts so as to be adapted to four or more medical connectors 20. Furthermore, although the medical connector coupling assisting tools 4 to 8 are respectively provided with the reinforcing ribs 4e to 8e, the number of reinforcing ribs 4e to 8e can be increased or reduced, and the reinforcing ribs 4e to 8e can be omitted. Similarly, although the medical connector coupling assisting tools 4 to 8 are respectively provided with the cuts 4f to 8f, the number of cuts 4f to 8f can be increased or reduced, and the cuts 4f to 8f can be omitted.

REFERENCE SIGNS LIST 1 medical connector coupling assisting tool
1a insertion part
1b claw part
1c coupling part
1d thick part
2 medical connector coupling assisting tool
2a insertion part
2b claw part
2d cutout
3 medical connector coupling assisting tool
3a insertion part
3c coupling part
3e projection
4 medical connector coupling assisting tool
4a insertion part
4c coupling part
4d thick part
4e reinforcing rib
4f cut
5 medical connector coupling assisting tool
5a insertion part
5c coupling part
5d thick part
5e reinforcing rib
5f cut
5g distal end region of insertion part
6 medical connector coupling assisting tool
6a insertion part
6c coupling part
6d thick part
6e reinforcing rib
6f cut
6g distal end region of insertion part
7 medical connector coupling assisting tool
7a insertion part
$7a_1$ one of two insertion parts
$7a_2$ the other of the two insertion parts
7c coupling part
7d thick part
7e reinforcing rib
7f cut
7g distal end region of insertion part
$7g_2$ distal end region of the other of the two insertion parts
8 medical connector coupling assisting tool
8a insertion part
8c coupling part
8d thick part
8e reinforcing rib
8f cut
8g distal end region of insertion part
8h overhanging part
9 medical connector coupling assisting tool
9a insertion part
9b pair of claw parts
9c coupling part
10 medical connector coupling assisting tool
10a insertion part
$10a_1$ one insertion part
$10a_2$ the other insertion part
10c coupling part
20 medical connector
21 operation lever
21a inside wall part
22 cylindrical body
23 male connector part
24, 24' female connector part
24a uneven part
25 mixed injection port
25a connection opening
25b valve body
25c flange part
26a right side vertical rib
26b left side vertical rib
26c pair of front side vertical ribs
26d pair of back side vertical ribs
27 cylinder part
30 T port
31 mixed injection port
32 male connector part
33 female connector part
34 barrel part
100 to 1000 medical connector set
L lock connector part
$O_1, O_2, O_3$ axis
$N_1$ first constriction part
$N_2$ second constriction part
$N_3$ third constriction part
$N_4$ constriction part of T port
$C_1$ first recessed part
$C_2$ second recessed part

What is claimed is:

1. A medical connector coupling assisting tool for use with a lock connector part interconnecting at least two medical connectors, each of which includes a constriction part, the medical connector coupling assisting tool comprising:

a coupling part that includes a front surface, a back surface, a first lateral surface, and a second lateral surface;

a first insertion part and a second insertion part, which are configured to be inserted into respective portions defined by the constriction parts such that the insertion parts are thereby detachably mounted on the constriction parts, wherein the first insertion part has a shape of an arc-shaped arm that extends in a first lateral direction from the first lateral surface of the coupling part, and the second insertion part has a shape of an arc-shaped arm that extends in a second lateral direction from the second lateral surface of the coupling part, the second lateral direction being opposite the first lateral direction; and an overhanging part connected to an edge of the coupling part and projecting frontwards from the edge of the coupling part.

2. A medical connector set comprising:

at least two medical connectors, each of which includes a constriction part;

a lock connector part interconnecting the at least two medical connectors; and the medial connector coupling assisting tool according to claim 1.

3. The medical connector set according to claim 2, wherein:

the constriction part of each medical connector is aligned in parallel with an axis of the lock connector part in an interconnected state.

4. The medical connector set according to claim 2, wherein:

the at least two medical connectors include a first medical connector and a second medical connector, the constriction part of the first medical connector is aligned in parallel with an axis of the lock connector part in an interconnected state, and the constriction part of the second medical connector is aligned perpendicular to the axis of the lock connector part in the interconnected state.

5. The medical connector set according to claim 2, wherein:

said portions defined by the constriction parts are recessed parts.

6. The medical connector set according to claim 5, wherein:

each of the constriction parts has an axis orthogonal to an axis of the lock connector part, and each recessed part defined by each respective constriction part is located around the axis of each respective constriction part, and each of the insertion parts is located across the axis of the lock connector part when viewed along the axis of the respective constriction part in a mounted state on the constriction part.

7. The medical connector set according to claim 2, wherein:

each of the medical connectors includes a mixed injection port to which another medical connector is capable of being coupled via a valve body, and each constriction part is formed at the respective mixed injection port.

8. The medical connector coupling assisting tool according to claim 1, wherein:

a thickness of each of the first and second insertion parts is less than a thickness of the coupling part.

9. The medical connector coupling assisting tool according to claim 8, wherein:

the first insertion part is offset toward the front surface of the coupling part, and the second insertion part is offset toward the back surface of the coupling part.

10. The medical connector coupling assisting tool according to claim 1, wherein:

the coupling part comprises:

a first rib that comprises the first lateral surface, the first rib protruding frontwards and extending in a direction perpendicular to the first lateral direction, and a second rib that comprises the second lateral surface, the second rib protruding frontwards and extending in a direction perpendicular to the second lateral direction.

11. The medical connector coupling assisting tool according to claim 1, wherein:

each insertion part includes at least one cut.

12. The medical connector coupling assisting tool according to claim 1, wherein:

each insertion part comprises a claw part that detachably locks the insertion part to a respective constriction part.

13. A medical connector coupling assisting tool for use with two lock connector parts interconnecting three medical connectors, each of which includes a constriction part, the medical connector coupling assisting tool comprising:

a plate member comprising three cutout parts defining three respective insertion parts configured to be inserted into respective portions defined by the constriction parts such that the insertion parts are thereby detachably mounted on the constriction parts; and two coupling parts formed integrally with adjacent insertion parts and coupling the adjacent insertion parts together, wherein outer insertion parts among the three insertion parts have a shape of an arc-shaped arm that extends from a first end that is located at a respective coupling part to a second end that is located away from the respective coupling part.

14. The medical connector coupling assisting tool according to claim 13, wherein the plate member has at least one reinforcing rib between the cutout parts, and the reinforcing rib extends perpendicular to an axis of the lock connector parts, with the insertion parts mounted on each respective constriction part.

15. The medical connector coupling assisting tool according to claim 13, wherein:

each insertion part includes at least one cut.

16. The medical connector coupling assisting tool according to claim 13, wherein:

each of the outer insertion parts has a claw part that detachably locks the insertion part to a respective constriction part.

17. A medical connector set comprising:

at least two medical connectors, each of which includes a constriction part;

a lock connector part interconnecting the at least two medical connectors; and the medial connector coupling assisting tool according to claim 13.

18. The medical connector set according to claim 17, wherein:

the constriction part of each medical connector is aligned in parallel with an axis of a respective lock connector part in an interconnected state.

19. The medical connector set according to claim 17, wherein:

said portions defined by the constriction parts are recessed parts.

20. The medical connector set according to claim 19, wherein:
- each of the constriction parts has an axis orthogonal to an axis of a respective lock connector part, and each recessed part defined by each respective constriction part is located around the axis of each respective constriction part, and
- each of the insertion parts is located across the axis of a respective lock connector part when viewed along the axis of the respective constriction part in a mounted state on the constriction part.

21. The medical connector set according to claim 17, wherein:
- each of the medical connectors includes a mixed injection port to which another medical connector is capable of being coupled via a valve body, and
- each constriction part is formed at the respective mixed injection port.

* * * * *